(12) United States Patent
Wild et al.

(10) Patent No.: US 7,311,916 B2
(45) Date of Patent: Dec. 25, 2007

(54) METHODS OF ELICITING BROADLY NEUTRALIZING ANTIBODIES TARGETING HIV-1 GP41

(75) Inventors: Carl T. Wild, Gaithersburg, MD (US); Carol D. Weiss, Bethesda, MD (US)

(73) Assignees: The Government of the United States of America, as represented by the Secretary, Department of Health and Human Services, Washington, DC (US); Panacos Pharmaceuticals, Inc., Gaitherburg, MD (US)

( * ) Notice: Subject to any disclaimer, the term of this patent is extended or adjusted under 35 U.S.C. 154(b) by 595 days.

(21) Appl. No.: 10/660,206

(22) Filed: Sep. 10, 2003

(65) Prior Publication Data

US 2004/0213801 A1 Oct. 28, 2004

Related U.S. Application Data

(63) Continuation of application No. 09/480,336, filed on Jan. 7, 2000, now abandoned.

(60) Provisional application No. 60/115,404, filed on Jan. 8, 1999.

(51) Int. Cl.
*A61K 39/21* (2006.01)
*A61K 39/385* (2006.01)
(52) U.S. Cl. ................. 424/188.1; 424/196.11
(58) Field of Classification Search ............. None
See application file for complete search history.

(56) References Cited

U.S. PATENT DOCUMENTS 5,464,933 A 11/1995 Bolognesi et al.
5,656,480 A 8/1997 Wild et al.
2001/0047080 A1 11/2001 Root et al.
2003/0082525 A1 5/2003 Root et al.

FOREIGN PATENT DOCUMENTS

WO WO 00/40616 7/2000
WO WO 03/052122 6/2003

OTHER PUBLICATIONS

The International Search Report dated Feb. 10, 2004.
Gruber, M. et al., "Study of Viral Replication in HIV-I-Infected CEM T-Cell Subclones Which Are Reduced in Their Ability to Form Syncytia," *AIDS Research and Human Retroviruses*, vol. 8, No. 6, pp. 1139-1146 (Jun. 1992).

(Continued)

*Primary Examiner*—Jeffrey S. Parkin
(74) *Attorney, Agent, or Firm*—Merchant & Gould P.C.

(57) ABSTRACT

The present invention is directed to the induction and characterization of a humoral immune response targeting "entry-relevant" gp41 structures. In its broadest aspect, the present invention is directed to methods of raising a neutralizing antibody response to a broad spectrum of HIV strains and isolates. The present invention targets particular molecular conformations or structures that occur at the cell surface of HIV during viral entry into host cells. Such a humoral response can be generated in vivo as a prophylactic measure in individuals to reduce or inhibit the ability of HIV to infect uninfected cells in the individual's body. Such a response can also be employed to raise antibodies against "entry relevant" gp41 structures. These antibodies can be employed for therapeutic uses, and as tools for further illuminating the mechanism of HIV cell entry.

16 Claims, 8 Drawing Sheets

OTHER PUBLICATIONS

Barin, F. et al., "Virus Envelope Protein of HTLV-III Represents Major Target Antigen for Antibodies in AIDS Patients", *Science*, 1094-1096 (May 1985).

Brodeur et al., "Mouse-Human Myeloma Partners for the Production of Heterohybridomas", *Monoclonal Antibody Production Techniques and Applications*, Marcel Dekker, Inc., New York, 33:51-63 (1987).

Caffrey et al., "Three-dimensional solution structure of the 44 kDa ectodomain of SIV gp41", *EMBO J.*, 17(16):4572-4584 (Aug. 17, 1998).

Caffrey et al., "Biophysical Characterization of gp41 Aggregates Suggests a Model for the Molecular Mechanism of HIV-associated Neurological Damage and Dementia", *J. Biol. Chem.*, 275(26):19877-19882 (Jun. 30, 2000).

Calderone, T. et al., "High-level Misincorporation of Lysine for Arginine at AGA Codons in a Fusion Protein Expressed in *Escherichia coli*", *J. Mol. Biol.*, 262:407-412 (Oct. 1996).

Cao J. et al., "Effects of Amino Acid Changes in the Extracellular Domain of the Human Immunodeficiency Virus Type I gp41", *Journal of Virology*, 67(5):2747-2755 (May 1993).

Chan, D. et al., "Evidence that a prominent cavity in the coiled coil of HIV type 1 gp41 is an attractive drug target", *Proc. Natl. Acad. Sci. USA*, 95:15613-15617 (Dec. 1998).

Chan et al., "Core Structure of gp41 from the HIV Envelope Glycoprotein", *Cell*, 89:263-273 (Apr. 18, 1997).

Chan et al., "HIV Entry and Its Inhibition", *Cell*. 93:681-684 (May 29, 1998).

Chen, C-H., et al., "A Molecular Clasp in the Human Immunodeficiency Virus (HIV) Type 1 TM Protein Determines the anti-HIV Activity of gp41 Derivatives: Implication for Viral Fusion", *J. Virol.*, 69:3771-3777 (Jun. 1995).

Clackson et al., "Making antibody fragments using phage display libraries", *Nature*, 352:624-628 (Aug. 15, 1991).

Connor, R. et al., "Vpr is Required for Efficient Replication of Human Immunodeficiency Virus Type-1 in Mononuclear Phagocytes", *Virology*, 206:935-944 (1995).

Cull, M.G., "Biotinylation of Proteins in Vivo and in Vitro Using Small Peptide Tags", *Methods Enzymol:*, 326:430-400 (2000).

de Rosny, E. et al., "Peptides Corresponding to the Heptad Repeat Motifs in the Transmembrane Protein (gp41) of Human Immunodeficiency Virus Type 1 Elicit Antibodies to Receptor-Activated Conformations of the Envelope Glycoprotein", *Journal of Virology*, 75(18):8859-8863 (Sep. 2001).

Doering, D. et al., "Cysteine Scanning Mutagenesis at 40 of 76 Positions in Villin Headpiece Maps the F-Actin Binding Site and Structural Features of the Domain", *Biochemistry*, 35:12677-12685 (1996).

Dong, X. et al., "N- and C-domains of HIV-1 gp41: mutation, structure and functions", *Immunology Letters*, 75:215-220 (2001).

Dwyer, J. et al., "The Hydrophobic Pocket Contributes to the Structural Stability of the N-Terminal Coiled Coil of HIV gp41 but Is Not Required for Six-Helix Bundle Formation", *Biochemistry*, 42:4945-4953 (2003).

Earl, P. et al., "Epitope Map of Human Immunodeficiency Virus Type 1 gp41 Derived from 47 Monoclonal Antibodies Produced by Immunization with Oligomeric Envelope Protein", *J. Virol.*, 71:2674-2684 (Apr. 1997).

Furuta, R. et al., "Capture of an early fusion-active conformation of HIV-1 gp41", *Nature Structural Biology*, 5(4):276-279 (Apr. 1998).

Goding, *Monoclonal Antibodies; Principles and Practice*, Academic Press, 59-103 (1983).

Golding et al., *Aids Res. Hum. Retroviruses*, 8:1607-1612 (1992).

Golding, H. et al., "LFA-1 Adhesion Molecules Are Not Involved in the Early Stages of HIV-1 *env*-Mediated Cell Membrane Fusion", *Aids Research and Human Retroviruses*, 8(9):1593-1598 (Sep. 1992).

Golding, H. et al., "Dissection of Human Immunodeficiency Virus Type 1 Entry with Neutralizing Antibodies to gp41 Fusion Intermediates", *Journal of Virology*, 76(13):6780-6790 (Jul. 2002).

He et al., "Peptides Trap the Human Immunodeficiency Virus Type 1 Envelope Glycoprotein Fusion Intermediate at Two Sites", *Journal of Virology*, 77(3):1666-1671 (Feb. 2003).

Holmes et al., "Bacteriophage Display of Chymotrypsin Inhibitor 2", *Protein Peptide Letters*, 3(6):415-422 (1996).

Jiang, S. et al., "HIV-1 inhibition by a peptide", *Nature*, 365:113 (Sep. 9, 1993).

Jiang, S. et al., "A Conformation-Specific Monoclonal Antibody Reacting with Fusion-Active gp41 from the Human Immunodeficiency Virus Type 1 Envelope Glycoprotein", *Journal of Virology*, 72(12):10213-10217 (Dec. 1998).

Jiang, S. et al., "Peptide and Non-peptide HIV Fusion inhibitors", *Current Pharmaceutical Design*, 8:563-580 (2002).

Jonak, Z. et al., "A Human Lymphoid Recombinant Cell Line with Functional Human Immunodeficiency Virus Type 1 Envelope", *AIDS Research Human Retroviruses*, 9(1):23-32 (Jan. 1993).

Kemble, G. et al., "Intermonomer Disulfide Bonds Impair the Fusion Activity of Influenza Virus Hemagglutinin", *J. Virol*, 66:4940-4950 (Aug. 1992).

Kilby, J. et al., "Potent suppression of HIV-1 replication in humans by T-20, a peptide inhibitor of gp41-mediated virus entry", *Nature Medicine*, 4(11):1302-1307 (Nov. 1998).

Kohler, G. et al., "Continuous cultures of fused cells secreting antibody of predefined specificity", *Nature*, 256:495-497 (Aug. 7, 1975).

Kozbor, D. et al., "A Human Hybrid Myeloma for Production of Human Monoclonal Antibodies", *Journal of Immunology*, 133(6):3001-3005 (Dec. 1984).

Laue, T. et al., "Analytical Ultracentrifugation in Biochemistry and Polymer Science", Harding, S.E., Rowe, A.J., and Horton, J. C., Eds., Royal Society for Chemistry, Cambridge, United Kingdom, pp. 90-125 (1992).

Lottenberg, R. et al., "Assay of Coagulation Proteases Using Peptide Chromogenic and Fluorogenic Substrates", *Methods in Enzymology*, 80:341-361 (1981).

Louis, J. et al., "Design and Properties of $N_{CCG}$-gp41, a Chimeric gp41 Molecule with Nanomolar HIV Fusion Inhibitory Activity", *Journal of Biological Chemistry*, 276(31):29485-29489 (2001).

Louis, J. et al., "Covalent Trimers of the Internal N-terminal Trimeric Coiled-coil of gp41 and Antibodies Directed against them are Potent Inhibitors of HIV Envelope-mediated Cell Fusion", *Journal of Biological Chemistry*, 278(22):20278-20285 (2003).

Lu, M. et al., "A trimeric structural domain of the HIV-1 transmembrane glycoprotein", *Nature Struct. Biol.*, 2:1075-1082 (Dec. 1995).

Lucic, M. et al., Secretion in *Escherichia coli* and phage-display of recombinant insulin-like growth factor binding protein-2, *Australia Journal of Biotechnology*, 61:95-108 (1998).

Lusso, P. et al., "Growth of Macrophage-Tropic and Primary Human Immunodeficiency Virus Type 1 (HIV-1) Isolates in a Unique $CD4^+$T-Cell Clone (PMI): Failure to Downregulate CD4 and to Interfere with Cell-Line-Tropic HIV-1", *Journal of Virology*, 69(6):3712-3720 (Jun. 1995).

Marks, J. et al., "By-passing Immunization: Human Antibodies from V-gene Libraries Displayed on Phage", *J. Mol. Biol.*, 222(3):581-597 (Dec. 5, 1991).

Matthews, D. et al., "Substrate Phage: Selection of Protease Substrates by Monovalent Phage Display", *Science*, 26:1113-1117 (1993).

Micheal, N. et al., "In vitro and in vivo characterization of a recombinant carboxypeptidase $G_2$::anti-CEA scFv fusion protein", *Immunotechnology*, 2:47-57 (1996).

Muster, T. et al., "A Conserved Neutralizing Epitope on gp41 of Human Immunodeficiency Virus Type 1", *J. Virol.*, 67:6642-6647 (Nov. 1993).

Muster, T. et al., "Cross-Neutralizing Activity against Divergent Human Immunodeficiency Virus Type 1 isolates induced by the gp41 Sequence ELDKWAS", *J. Virol.*, 68:4031-4034 (Jun. 1994).

Root, M. et al., "Protein Design of an HIV-1 Entry Inhibitor", *Science*, 291:884-888 (Feb. 2, 2001).

Sattentau, Q. et al., "Conformational Changes Induced in the Human Immunodeficiency Virus Envelope Glycoprotein by Soluble CD4 Binding", *J. Exp. Med.*, 174:407-415 (Aug. 1991).

Sattentau, T. et al., "Human Immunodeficiency Virus Type 1 Neutralization is Determined by Epitope Exposure on the gp120 Oligomer", *J. Exp. Med.*, 182:185-196 (Jul. 1995).

Studier, F. et al., "Use of T7 RNA Polymerase to Direct Expression of Cloned Genes" *Method in Enzymology*, 185:60-89 (1990).

Tan, K. et al., "Atomic structure of a thermostable subdomain of HIV-1 gp41", *Proc. Natl. Acad. Sci. USA*, 94:12303-12308 (Nov. 1997).

Tracy, P. et al., "Platelet Factor Xa Receptor", *Methods in Enzymology*, 215:329-360 (1992).

VanCott, T. et al., "Antibodies with Specificity to Native gp120 and Neutralization Activity against Primary Human Immunodeficiency Virus Type 1 isolates Elicited by Immunization with Oligomeric gp160", *J. Virol.*, 71:4319-4330 (Jun. 1997).

Weiss, C. et al., "Studies of HIV-1 envelope glycoprotein-mediated fusion using a simple fluorescence assay", *AIDS*, 10:241-246 (1996).

Weissenhorn, W. et al., "Atomic structure of the ectodomain from HIV-1 gp41", *Nature*, 387:426-430 (May 1997).

Weng, Y. et al., " Mutational Analysis of Residues in the Coiled-Coil Domain of Human Immunodeficiency Virus Type 1 Transmembrane Protein gp41", *Journal of Virology*, 72(12):9676-9682 (Dec. 1998).

White, J. et al., "Anti-Peptide Antibodies Detect Steps in a Protein Conformational Change: Low pH Activation of the Influenza Virus Hemagglutinin", *J. Cell Biol.*, 105:2887-1896 (Dec. 1987).

Wild, C. et al., "A Synthetic Peptide from HIV-1 gp41 is a Potent Inhibitor of Virus-Mediated Cell-Cell Fusion", *AIDS Res. Hum. Retroviruses*, 9:1051-1053 (Nov. 1993).

Wild, C. et al., "The inhibitory Activity of an HIV Type 1 Peptide Correlates with its Ability to Interact with a Leucine Zipper Structure", *AIDS Res. Hum. Retroviruses*, 11:323-325 (Mar. 1995).

Wild, C. et al., "A synthetic peptide inhibitor of human immunodeficiency virus replication: Correlation between solution structure and viral inhibition", *Proc. Natl. Acad. Sci. USA*. 89:10537-10541 (Nov. 1992).

Wild, C. et al., "Peptides corresponding to a predictive α-helical domain of human immunodeficiency virus type 1 gp41 are potent inhibitors of virus infection", *Proc. Natl. Acad. Sci. USA*, 91:9770-9774 (Oct. 1994).

Wild, C. et al., "Propensity for a leucine zipper-like domain of human immunodeficiency virus type 1 gp41 to form oligomers correlates with a role in virus-induced fusion rather than assembly of the glycoprotein complex", *Proc. Natl. Acad. Sci. USA*, 91:12676-12680 (Dec. 1994).

Wingfield, P. et al., "The extracellular domain of immunodeficiency virus gp41 protein: Expression in *Escherichia coli*, purification, and crystallization", *Protein Science*, 6:1653-1660 (1997).

Wung, J. et al., "Selection of phage-displayed superantigen by binding to cell-surface MHC class II", *Journal of Immunological Methods*, 204(1):33-41 (1997).

Xu, J-Y et al., "Epitope Mapping of Two Domains of gp41, the Transmembrane Protein of Human Immunodeficiency Virus Type 1, Using Ten Human Monoclonal Antibodies", *J. Virol.*, 65:4832-4838 (Sep. 1991).

International Search Report mailed Jun. 6, 2000.

OXIDATION & OLIGOMERIZATION OF MODIFIED P-17 TO FORM STABILIZED COILED-COIL STRUCTURE

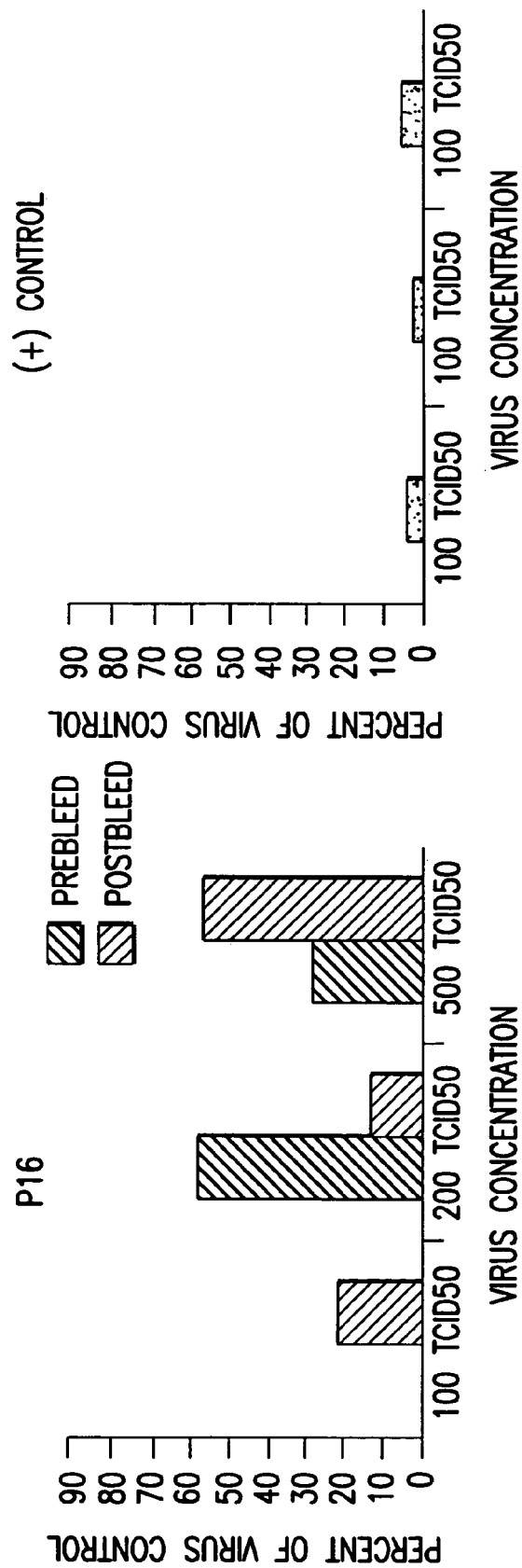

GAGGGACTATATCCGGTTATTCACAAGGACGGCTGTGGGCGCCATGATCGCGTAGTCGATAGTGGCT
CCAAGTAACCGGAAGCGACAGGGACTGTGCCGGGCGCCAAAGGCGGTCGACAGTGCTTTCTAGAACC
GGGTGCGCATAAAAATGCATCACGCCTATAGCGCTAGAGCCGCTGCATTAAATGAATCGGCCA

BN11/107-178F PRIMER   107+178Stop

AGCGGTGCGCCGAAAGTACGCGCTAAG CTT CAT ATG GGT ATT GTT CAG CAG CAG AAC
                                         M   G   I   V   Q   Q   Q   N
AAT TTG CTG AGG GCT ATT GAG GCG CAA CAG CAC CTG CTG CAG CTG ACC GTA
 N   L   R   A   I   E   A   Q   Q   H   L   L   Q   L   T   V
TGG GGC ATC AAG CAG CTG CAG GCA CGC ATC CTG GCT GTT GAA CGC TAC CTG
 W   G   I   K   Q   L   Q   A   R   I   L   A   V   E   R   Y   L
AAG GAT CAA GGC GGC GGC TCA GGC GCC GGC TCA GAG TGG GAC AGA GAA ATT
 K   D   Q   G   G   G   S   G   A   G   S   E   W   D   R   E   I
AAC AAT TAC ACA AGC TTA ATA CAC TCC TTA ATT GAA GAA TCG CAA AAC CAG
 N   N   Y   T   S   L   I   H   S   L   I   E   E   S   Q   N   Q
CAA GAA AAG AAT GAA CAA GAA TTA TTG GAA TTA GAT AAA TGG GCA AGT TTG
 Q   E   K   N   E   Q   E   L   L   E   L   D   K   W   A   S   L
TGG AAT TGG TTT GAA TTC ATC GAT GAT ATC AGA TCC GGC TGC TAA CAA AGC
 W   N   W   F   E   F   I   D   D   I   R   S   G   C   STOP
CCG AAA GGA AGC TGA GTT TGG CTG CTG CCA CCC GCT GAG CAA TAA CTA GCA

TAA CCC CTT GGG GGC CTC TAA ACG GGT CTT GAG GGG TTT TTT GCT TGA AAG

FIG. 7

METHODS OF ELICITING BROADLY NEUTRALIZING ANTIBODIES TARGETING HIV-1 GP41

CROSS-REFERENCE TO RELATED APPLICATIONS

This application is a continuation application of U.S. application Ser. No. 09/480,336 filed Jan. 7, 2000, now abandoned, which application claims priority benefit under 35 U.S.C. § 119(e) to U.S. Provisional Application No. 60/115,404 filed Jan. 8, 1999, the entire contents of which is incorporated herein by reference.

STATEMENT AS TO RIGHTS TO INVENTIONS MADE UNDER FEDERALLY-SPONSORED RESEARCH AND DEVELOPMENT

Part of the work performed during development of this invention utilized U.S. Government funds. The U.S. Government has certain rights in this invention pursuant to INNOVATION Grant No. R21 AI 42714.

BACKGROUND OF THE INVENTION

1. Field of the Invention

The present invention is related to HIV therapy and prophylaxis. In particular, the invention relates to methods for eliciting broadly neutralizing antibodies that target entry-relevant structures of HIV-1 gp41. Such methods, and pharmaceutical compositions therefor, can be employed to inhibit HIV entry into uninfected cells.

2. Related Art

The development of effective vaccines to prevent infection with HIV remains a high priority goal. To date, envelope glycoproteins (gp160 and gp120/gp41) have been the main focus of vaccine research efforts. One result of this work is the observation that the humoral response generated against native forms of the envelope (primarily oligomeric forms of the gp120/gp41 complex) is more broadly neutralizing than antibody raised against denatured and/or monomeric envelope (VanCott, T. C., et al., *J. Virol.* 71:4319-4330 (1997)). Structural considerations are important components for both understanding the immunogenicity of the envelope protein and the design of envelope based immunogens which induce a broad neutralizing response against HIV.

A good deal of structural information is available with respect to the transmembrane protein (TM or gp41). Predictive work indicated that several regions of the ectodomain of gp41 display a high propensity to exhibit certain specific types of secondary structure (Gallaher, W. R., et al., *AIDS Res. Hum. Retroviruses* 5:431-440 (1989); Delwart, E. L., et al., *AIDS Res. Hum. Retroviruses* 6:703-704 (1990)). Experimental work employing both synthetic peptides and protein recombinants has established that these predictions were generally correct and recently a three dimensional structure for a portion of the gp41 ectodomain was reported (Wild, C., et al., *Proc. Natl. Acad. Sci. USA* 89:10537-10541 (1992); Wild, C., et al., *Proc. Natl. Acad. Sci. USA* 91:12676-12680 (1994); Wild, C., et al., *AIDS Res. Hum. Retroviruses* 11:323-325 (1995); Chan, D. C., et al, *Cell* 89:263-273 (1997)). Results from both solution studies and crystallographic analysis indicate that in one form this structured region of the transmembrane protein is a primer of two interacting regions of gp41. This trimeric structure is a six helix bundle consisting of an interior parallel coiled-coil primer (region one) which associates with three identical α-helices (region two) which pack in an oblique, antiparallel manner into the hydrophobic grooves on the surface of the coiled-coil trimer (FIG. 3). This hydrophobic self-assembly domain is believed to constitute the core structure of gp41.

A series of studies carried out using both synthetic peptides and recombinant proteins modeling the distal regions of the TM involved in generating this structure suggest that it (or the gp41 regions from which it is derived) plays a critical role in the process of HIV-1 entry (Wild, C., et al., *Proc. Natl. Acad. Sci. USA* 89:10537-10541 (1992); Wild, C., et al., *AIDS Res. Hum. Retroviruses* 9:1051-1053 (1993); Wild, C., et al., *Proc. Natl. Acad. Sci. USA* 91:12676-12680 (1994); Wild, C., et al., *AIDS Res. Hum. Retroviruses* 11:323-325 (1995); Wild, C., et al., *Proc. Natl. Acad. Sci. USA* 91:9770-9774 (1994); Chen, C. -H., et al., *J. Virol.* 69:3771-3777 (1995)).

The functional role of the transmembrane protein of HIV-1 in virus replication was shown when the region of the ectodomain of the TM corresponding to amino acid residues 558-595, which was predictive of α-helical secondary structure (Gallaher, W. R., et al., *AIDS Res. Hum. Retroviruses* 5:431-440 (1989); Delwart, E. L., et al., *AIDS Res. Hum. Retroviruses* 6:703-704 (1990)), formed a coiled-coil structure when modeled as a synthetic peptide (Wild, C., et al., *Proc. Natl. Acad. Sci. USA* 89:10537-10541 (1992)). The peptide modeling this region, DP-107, was shown to be a potent, virus specific inhibitor of HIV replication and the inhibitory activity was related to the structural components exhibited by the peptide. In both neutralization and cell-cell fusion assays, the DP-107 peptide completely blocked virus infection at concentrations of 1.0 μg/ml. Unlike other inhibitors of HIV replication (i.e. soluble CD4) and most neutralizing sera, the activity of the DP-107 peptide was not isolate restricted. Using a series of DP-107 analogs containing structure disrupting point mutations and a set of HIV-1 envelope constructs containing identical mutations, it has been shown that the structural components of the coiled-coil region of the TM were critical to both virus entry and fusion phenotype and that mutations which disrupted this gp41 structure gave rise to an envelope complex which was unable to mediate virus entry (Wild, C., et al., *Proc. Natl. Acad. Sci. USA* 91:12676-12680 (1994)).

Studies of the coiled-coil domain of gp41 resulted in the identification of a second region of the ectodomain of the TM, which when modeled as a synthetic peptide, was also a potent, virus specific inhibitor of HIV replication (Wild, C., et al., *AIDS Res. Hum. Retroviruses* 9:1051-1053 (1993)). However, unlike the DP-107 region, the peptide corresponding to amino acid residues 643-678 of the TM (DP-178), did not exhibit stable solution structure. Experiments with the DP-107 and DP-178 peptides established that both of these materials blocked HIV replication at an early step, most likely during virus entry (Wild, C., et al., *Proc. Natl. Acad. Sci. USA* 91:9770-9774 (1994)). This observation led to speculation that these peptides might inhibit virus replication by interacting with and disrupting determinants within the TM that were critical for virus entry. Efforts to better define the higher order structural components that were present in gp41 and functioned during virus entry led to the observation that the distal regions of the TM modeled by the two inhibitory peptides (DP-107 and DP-178) did interact with one another to form an oligomeric structure (Wild, C., et al., *AIDS Res. Hum. Retroviruses* 11:323-325 (1995); Chen, C. -H., et al., *J. Virol.* 69:3771-3777 (1995)). Recently, this oligomeric structure was characterized as a trimeric, six helix bundle consisting of an interior parallel coiled-coil trimer (DP-107 region) which associates with three identical α-helices (DP-178 region) which pack into the hydrophobic grooves on the surface of the coiled-coil trimer (FIG. 3) (Chan, D. C., et al., *Cell* 89:263-273 (1997)).

Research has focused on determining the functional role of these gp41 structural determinants in virus entry. DP-107 and DP-178 peptides interact in a specific manner with the ectodomain of gp41 and this interaction is critical to their inhibitory activities.

U.S. Pat. No. 5,464,933, Bolognesi et al., describes peptides which exhibit potent anti-retroviral activity. Specifically disclosed are the peptide DP-178 (SEQ ID NO:3) derived from the HIV-1$_{LAI}$ gp41 protein, as well as fragments, analogs and homologs of DP-178. The peptides are used as direct inhibitors of human and non-human retroviral transmission to uninfected cells. The patent teaches that the peptides may also be prophylactically employed in individuals after such individuals have had an acute exposure to HIV.

U.S. Pat. No. 5,656,410, Wild et al., describes protein fragments derived from the HIV transmembrane glycoprotein (gp41), including the peptide DP-107 (SEQ. ID NO:1) which have antiviral activity. Also disclosed are methods for inhibiting enveloped viral infection, and methods that modulate biochemical processes involving coiled coil peptide interactions.

While recent work has increased knowledge of the structural components of the HIV-1 transmembrane protein, the immunogenic nature of gp41 remains poorly understood. It is known that one of two immunodominant regions present in the HIV-1 envelope complex is located in gp41 (Xu, J. -Y., et al., *J. Virol.* 65:4832-4838 (1991)). This determinant (TM residues 597-613) is associated with a strong, albeit non-neutralizing humoral response in a large number of HIV+ individuals. Also, the broadly neutralizing antibody, 2F5, maps to the ectodomain of gp41 (TM residues 662-667) (Muster, T., et al., *J. Virol.* 67:6642-6647 (1993); Muster, T., et al., *J. Virol.* 68:4031-4034 (1994)). It is interesting to note that this antibody maps to a determinant of the TM that overlaps one of the two regions of gp41 which interact to form the recently characterized hydrophobic core of the protein (FIG. 1). This observation has lead to speculation that 2F5 might actually neutralize virus by interacting with and disrupting the function of an entry-relevant gp41 structure. An extensive study which mapped the antigenic structure of gp41 supports this idea. This work characterized several conformation dependent gp41 MAbs which mapped to the same region of the TM as 2F5 (Earl, P. L., et al., *J. Virol.* 71:2647-2684 (1997)). Although the binding sites for these non-neutralizing monoclonal antibodies (MAbs) overlapped the 2F5 determinant, in competition experiments neither of these antibodies was blocked from binding to native protein by the 2F5 MAb. This indicates that while the two dimensional regions to which these antibodies map are similar, the three dimensional epitopes to which they bind are quite different.

The observation that only one neutralizing MAb (2F5) maps to the ectodomain of gp41 and that antibodies to the 2F5 epitope are poorly represented in sera from HIV infected individuals suggests that, for the most part, gp41 neutralizing epitopes are cryptic. The cryptic nature of these neutralizing epitopes is most likely related to the functional role of the TM in HIV-1 replication which involves mediating virus entry. It has been shown that prior to gp120-CD4 binding the HIV envelope complex exists in a non-fusogenic form. While the exact nature of this pre-entry form is unknown, binding experiments have established that the non-fusogenic state is characterized by the inaccessibility of large portions of the gp41 ectodomain (Sattentau, Q. J. and J. P. Moore, *J. Exp. Med.* 174:407-415 (1991); Sattentau, Q. J., et al., *Virol.* 206:713-717 (1995)). However, once binding of virus to target cell has occurred, the gp120-gp41 complex undergoes a series of conformational changes that involve reorganization of both the extracellular surface component of the HIV-1 envelope protein (SU or gp120) and TM proteins and the formation of structural components within the TM which are believed to be critical to virus entry. Although the steps involved in the transition from the non-fusogenic to fusogenic state are largely unknown, it is believed that this transformation is characterized by the formation of a series of structural intermediates within the transmembrane protein which drive the conformational changes required for virus entry. The transitory nature of this event and the structures associated with it, rather than the absence of appropriate structural determinants, are believed to account for the poor neutralizing response to the TM component of the envelope system.

Attention has been given to the development of vaccines for the treatment of HIV infection. The HIV-1 envelope proteins (gp160, gp120, gp41) have been shown to be the major antigens for anti-HIV antibodies present in AIDS patients (Barin, et al., *Science* 228:1094-1096 (1985)). Thus far, these proteins seem to be the most promising candidates to act as antigens for anti-HIV vaccine development. To this end, several groups have begun to use various portions of gp160, gp120, and/or gp41 as immunogenic targets for the host immune system. However, prior art attempts have thus far met with minimal success.

Thus, although a great deal of effort is being directed to the design and testing of HIV vaccines, an effective vaccine is needed.

SUMMARY OF THE INVENTION

An objective of the present invention is the induction and/or characterization of a humoral immune response targeting "entry-relevant" gp41 structures. In its broadest aspect, the present invention is directed to methods of raising a neutralizing antibody response to a broad spectrum of HIV strains and isolates. The present invention targets particular molecular conformations or structures that occur, or are exposed, following interaction of HIV with the cell surface during viral entry. Such a humoral response can be generated in vivo as a prophylactic or therapeutic measure in individuals to reduce or inhibit the ability of HIV to infect uninfected cells in the individual's body. Such a response can also be employed to raise antibodies against "entry relevant" gp41 structures. These antibodies can be subsequently employed for therapeutic uses, and as tools for further illuminating the mechanism of HIV cell entry.

One aspect of the present invention relates to a method of raising a broadly neutralizing antibody response to HIV by administering to a mammal a peptide or polypeptide comprising an amino acid sequence that is capable of forming a stable coiled-coil solution structure corresponding to or mimicking the heptad repeat region of gp41, (or the N-helical domain of gp41). Peptides of this aspect of the invention are exemplified by P-15 and P-17 described herein.

A second aspect of the present invention relates to a method of raising a broadly neutralizing antibody response to HIV by administering to a mammal a peptide or polypeptide comprising an amino acid sequence that corresponds to, or mimics, the transmembrane-proximal amphipathic α-helical segment of gp41 (at the C-helical domain of gp41), or a portion thereof. Peptides of this aspect of the invention are exemplified by P-16 and P-18 described herein.

A third aspect of the present invention relates to a method of raising a broadly neutralizing antibody response to HIV by administering to a mammal a composition including one or more peptides or polypeptides which comprise amino acid sequences that are capable of forming solution stable structures that correspond to, or mimic, the gp41 core six helix bundle. This bundle forms in gp41 by the interaction of the distal regions (N-helical domain and C-helical domain) of the transmembrane protein. See FIG. 1. This aspect of the invention is also directed to novel mixtures of peptides and polypeptides, including multimeric and conjugate structures, wherein said mixtures and structures form a stable core helix solution structure. A preferred embodiment of this aspect of the invention involves raising antibodies to a physical mixture of N-helical domain peptide and C-helical domain peptide, for example, P-17 and P-18, P-15 and P-16, P-17 and P-16, or P-15 and P-18.

The present invention is also directed to a method of raising a broadly neutralizing antibody response to HIV by administering to a mammal a composition including one or more novel peptides and proteins, herein referred to as conjugates, that mimic fusion-active transmembrane protein structures. These conjugates are formed from two or more amino acid sequences that comprise:

(a) one or more amino acid sequences that are capable of forming a stable coiled-coil solution structure corresponding to or mimicking the heptad repeat region of gp41 (N-helical domain); and (b) one or more amino acid sequences that correspond to, or mimic, an amino acid sequence of the transmembrane-proximal amphipathic α-helical segment of gp41 (C-helical domain);

wherein said one or more sequences (a) and (b) are alternately linked to one another via a bond, such as a peptide bond (amide linkage) or by an amino acid linking sequence consisting of about 2 to about 25 amino acids. These conjugates are preferably recombinantly produced. An example of such a conjugate is described in Example 5.

In a preferred embodiment of this aspect of the invention, one or more of these conjugates folds and assembles in solution into a structure corresponding to, or mimicking, the gp41 core six helix bundle.

The present invention also relates to methods for forming peptides, multimers and conjugates of the invention.

The present invention also relates to pharmaceutical compositions comprising the peptides, multimers and conjugates of the invention and a pharmaceutical acceptable carrier.

The present invention also relates to polyclonal and monoclonal antibodies that are raised to the peptides, multimers and conjugates described in the preceding paragraphs.

The present invention also relates to a method of administering a composition comprising polyclonal or monoclonal antibodies described above to an individual in an amount effective to reduce HIV infection of uninfected cells.

The present invention also relates to a vaccine for providing a protective response in an animal comprising one or more peptides, multimers or conjugates of the present invention together with a pharmaceutically acceptable diluent, carrier, or excipient, wherein the vaccine may be administered in an amount effective to elicit an immune response in an animal to HIV. In a preferred embodiment, the animal is a mammal. In another preferred embodiment, the mammal is a human.

BRIEF DESCRIPTION OF THE FIGURES

FIG. 6: Percent neutralization for gp233 and gp234 sera in different experimental formats.

FIG. 7 provides an example of a construct of the present invention (SEQ. ID NO:75) along with the corresponding nucleic acid sequence used for recombinant expression of the construct (SEQ. ID NO:76).

DETAILED DESCRIPTION OF THE PREFERRED EMBODIMENTS

Figure 1:
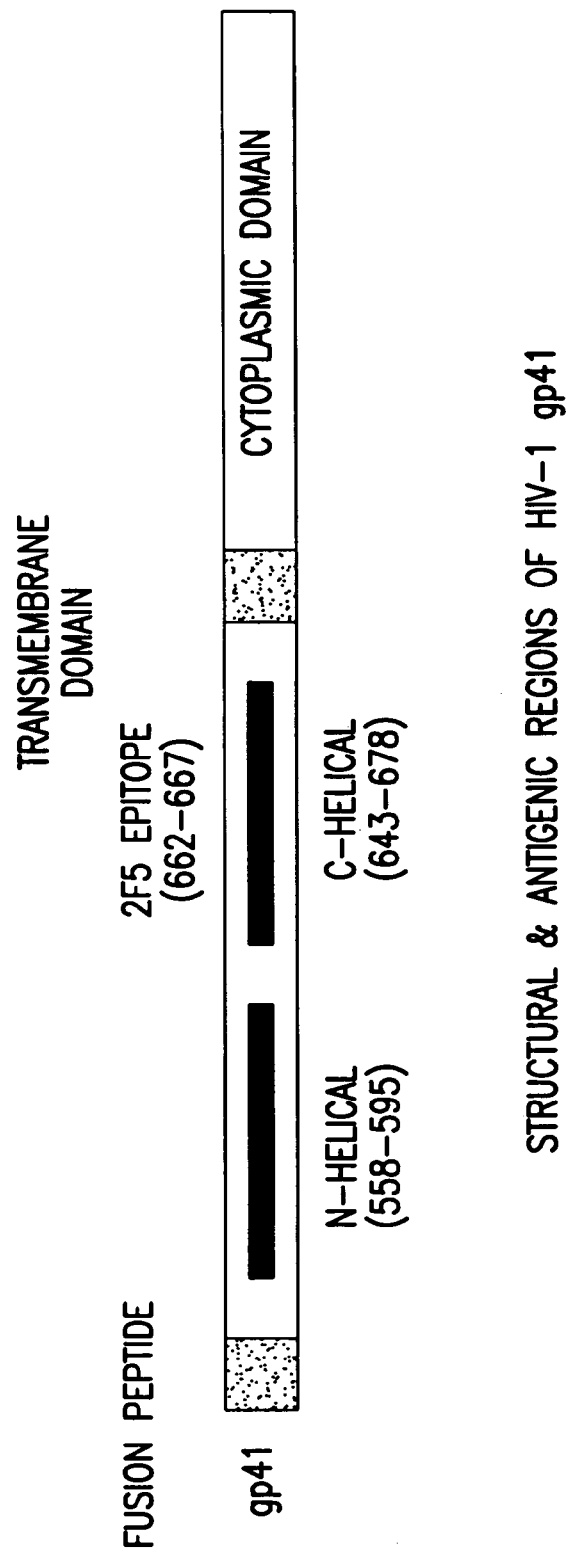
FIG. 1 illustrates the structural and antigenic regions of HIV-1 gp41. The extracellular, transmembrane and cytoplasmic domains are shown, as are the transmembrane-proximal amphipathic α-helical segment of gp41 (C-helical domain) and the heptad repeat region of gp41 (N-helical domain).

The transitory-nature of the HIV-entry event, and the structures associated with it, account for the seeming lack of neutralizing epitopes within gp41. These structural components, which form and function only during virus entry, and remain unexposed or are not present in the "native" fusion-inactive envelope complex, constitute a novel set of neutralizing epitopes within gp41. The present invention involves immunization with constructs mimicking these highly conserved, gp41 structures involved in virus entry to elicit the production of broadly neutralizing antibodies targeting these structures. Thus, this invention is the induction of a humoral immune response targeting these "entry relevant" gp41 structures.

One aspect of the present invention relates to a method of raising a broadly neutralizing antibody response to HIV by administering to a mammal a peptide or polypeptide comprising an amino acid sequence that is capable of forming a stable coiled-coil solution structure corresponding to or mimicking the heptad repeat region of gp41 which is located in the N-helical domain as defined herein. Peptides, or multimers thereof, that comprise amino acid sequences which correspond to or mimic solution conformation of the heptad repeat region of gp41 can be employed in this aspect of the invention. The heptad repeat region of gp41 includes 4 heptad repeats. Preferably, the peptides comprise about 28 to 55 amino acids of the heptad repeat region of the extracellular domain of HIV gp41 (N-helical domain, (SEQ. ID NO:1)), or multimers thereof. The peptides can be administered as a small peptide, or conjugated to a larger carrier protein such as keyhole limpet hemocyanin (KLH), ovalbumin, bovine serum albumin (BSA) or tetanus toxoid.

Alternatively, peptides forming a stable coiled-coil solution structure corresponding to or mimicking the heptad repeat region of gp41 can be employed to form polyclonal or monoclonal antibodies that can be subsequently administered as therapeutic or prophylactic agents.

To determine whether a particular peptide or multimer will possess a stable trimeric coiled-coil solution structure corresponding to or mimicking the heptad repeat region of gp41, the peptide can be tested according to the methods described in Wild, C., et al., *Proc. Natl. Acad. Sci. USA* 89:10537-10541 (1992), fully incorporated by reference herein.

Shown below is the sequence for residues of the HIV-1$_{LAI}$ gp41 protein that form the N-helical domain of the protein:

These peptides are optionally coupled to a larger carrier protein, or optionally include a terminal protecting group at the N- and/or C-termini. Useful peptides further include peptides corresponding to P-17 or P-15 that include one or more, preferably 1 to 10 conservative substitutions, as described below. A number of additional useful N-helical region peptides are described in the section entitled "Peptides."

A second aspect of the present invention relates to a method of raising a broadly neutralizing antibody response to HIV by administering to a mammal a peptide or polypeptide comprising an amino acid sequence that corresponds to, or mimics, the transmembrane-proximal amphipathic α-helical segment of gp41 (C-helical domain, (SEQ ID NO:4)), or a portion thereof. Useful peptides or polypeptides include an amino acid sequence that is capable of forming a core six helix bundle when mixed with a peptide corresponding to the heptad repeat region of gp41, such as the peptide P-17. Peptides can be tested for the ability to form a core six helix bundle employing the system and conditions described in Chan, D. C., et al, *Cell* 89:263-273 (1997); Lu, M., et al., *Nature Struct. Biol.* 2:1075-1082 (1995), fully incorporated by reference herein.

Shown below is the amino acid sequence for residues of the HIV-1$_{LAI}$ gp41 protein that form the C-helical domain of the protein:

```
WNNMTWMEWDREINNYTSLIHSLIEESQNQQEKNEQELLELDKWASLWNWFNITNW    (SEQ ID NO:4)
```

Preferred peptides or multimers thereof, that can be employed in this aspect of the invention comprise about 6 or more amino acids, preferably about 24-56 amino acids, of the extracellular C-helical domain of HIV gp41. The peptides can be administered as a small peptide, or conjugated to a larger carrier protein such as keyhole limpet hemocyanin (KLH), ovalbumin, bovine serum albumin (BSA) or tetanus toxoid. This transmembrane-proximal amphipathic α-helical segment is exemplified by the peptides P-16 and P-18, described below.

```
ARQLLSGIVQQQNNLLRAIEAQQHLLQLTVWGIKQLQARILAVERYLKDQQLLGI    (SEQ. ID NO:1)
```

Two examples of useful peptides include the peptide P-17, which has the formula, from amino terminus to carboxy terminus, of:

Alternatively, peptides or polypeptides comprising amino acid sequences that correspond to, or mimic, the transmembrane-proximal amphipathic α-helical segment of gp41, or a

```
NH₂-NNLLRAIEAQQHLLQLTVWGIKQLQARILAVERYLKDQ-COOH;    (SEQ ID NO:2)
``` and the peptide P-15, which has the formula, from amino terminus to carboxy terminus, of:

```
NH₂-SGIVQQQNNLLRAIEAQQHLLQLTVWGIKQLQARIL-COOH.    (SEQ ID NO:3)
``` portion thereof, can be employed to form polyclonal or monoclonal antibodies as therapeutic or prophylactic agents.

Examples of useful peptides for this aspect of the invention include the peptide P-18 which corresponds to a portion of the transmembrane protein gp41 from the HIV-1$_{LAI}$ isolate, and has the 36 amino acid sequence (reading from amino to carboxy terminus):

```
NH2-YTSLIHSLIEESQNQQEKNEQELLELDKWASLWNWF-COOH;   (SEQ ID NO:5)
``` and the peptide P-16, which has the following amino acid sequence (reading from amino to carboxy terminus):

```
NH2-WMEWDREINNYTSLIHSLIEESQNQQEKNEQELL-COOH    (SEQ ID NO:6)
```

These peptides are optionally coupled to a larger carrier protein. Useful peptides further include peptides corresponding to P-18 or P-16 that include one or more, preferably 1 to 10 conservative substitutions, as described below. In addition to the full-length P-18, 36-mer and the full length P-16, the peptides of this aspect of the invention may include truncations of the P-18 and P-16, as long as the truncations is capable of forming a six helix bundle when mixed with P-17. A number of other useful peptides are described in the section entitled "Peptides," below.

A third aspect of the present invention relates to a method of raising a broadly neutralizing antibody response to HIV by administering to a mammal a composition including one or more peptides or polypeptides which comprise amino acid sequences that are capable of forming solution stable structures that correspond to, or mimic, the gp41 core six helix bundle. This bundle forms in gp41 by the interaction of the distal regions of the transmembrane protein, the heptad repeat region and the amphipathic α-helical region segment roughly corresponding to the N-helical domain and C-helical domain. See FIG. 1. The bundle structures that form in native virus are the result of a trimeric interaction between three copies each of the heptad repeat region and the transmembrane-proximal amphipathic α-helical segment. In the compositions of the present invention, peptide regions interact with one another to form a core six helix bundle. This aspect of the invention is also directed to novel mixtures of peptides and polypeptides, including multimeric and conjugate structures, wherein said structures form a stable core helix solution structure.

This aspect of the invention can employ mixtures of (a) one or more peptides that comprise an amino acid sequence that corresponds to, or mimics, a stable coiled coil heptad repeat region of gp41; and (b) one or more peptides that comprise a region that corresponds to, or mimics, the transmembrane-proximal amphipathic α-helical segment of gp41. These mixtures are optionally chemically or oxidatively cross-linked to provide additional immunogenic structures that may or may not be solution stable. In addition to physical mixtures, and conventional cross-linking, the peptides (a) and (b) can be conjugated together via suitable linking groups, preferably a peptide residue having at least 2, preferably 2 to 25, amino acid residues. Preferred linking groups are formed from combinations of glycine and serine, or combinations of glycine and cysteine when further oxidative cross-linking is envisioned.

A preferred embodiment of this aspect of the invention involves raising antibodies to physical mixtures of P-17 and P-18, P-15 and P-16, P-17 and P-16 or P-15 and P-18.

The present invention is also directed to a method of raising a broadly neutralizing antibody response to HIV by administering to a mammal a composition including one or more novel peptides and proteins, herein referred to as conjugates, that mimic fusion-active transmembrane protein structures. These conjugates are formed from peptides and proteins that comprise:

(a) one or more amino acid sequences of 28 or more amino acids that are capable of forming a stable coiled-coil solution structure corresponding to or mimicking the heptad repeat region of gp41; and (b) one or more amino acid sequences that correspond to, or mimic, an amino acid sequence of the transmembrane-proximal amphipathic α-helical segment of gp41;

wherein said one or more sequences (a) and (b) are alternately linked to one another via a peptide bond (amide linkage) or by an amino acid linking sequence consisting of about 2 to about 25 amino acids. These peptides and proteins are preferably recombinantly produced.

In a preferred embodiment of this aspect of the invention, one or more of these conjugates folds and assembles into a structure corresponding to, or mimicking, the gp41 core six helix bundle.

Non-limiting examples of the novel constructs or conjugates that can be formed include:

(1) three tandem repeating units consisting of P-17-linker-P-18 (P-17-linker-P-18-linker-P-17-linker-P-18-linker-P-17-linker-P-18), (2) P-17-linker-P-18-linker-P-17, (3) P-18-linker-P-17-linker-P-18, (4) P-17-linker-P-17, (5) three tandem repeating units consisting of P-15-linker-P-16 (P-15-linker-P-16-linker-P-15-linker-P-16-linker-P-15-linker-P-16), (6) P-15-linker-P-16-linker-P-15, (7) P-16-linker-P-15-linker-P-16, and (8) P-16-linker-P-15;

wherein each linker is an amino acid sequence, which may be the same or different, of from about 2 to about 25, preferably 2 to about 16 amino acid residues. Preferred amino acid residues include glycine and serine, for example (GGGGS)$_x$, (SEQ ID NO:7) wherein x is 1, 2, 3, 4, or 5, or glycine and cysteine, for example (GGC)y, where y is 1, 2, 3 4 or 5. In any of the described constructs, P-15 and P-17 are interchangeable and P-16 and P-18 are interchangeable. An example of such a construct (SEQ ID NO:77) is shown in FIG. 7, along with the corresponding nucleic acid sequence (SEQ ID NO:78) used for recombinant expression of the construct.

Alternatively, polyclonal or monoclonal antibodies can be raised against the immunogenic mixtures and conjugates described in this aspect of the invention. Such antibodies can be employed as therapeutic or prophylactic agents.

In preferred aspects of the invention, the methods can be employed to immunize an HIV-1-infected individual such that levels of HIV-1 will be reduced in such individual. In another aspect, the methods can be employed to immunize a non-HIV-1-infected individual so that, following a subsequent exposure to HIV-1 that would normally result in HIV-1 infection, the levels of HIV-1 will be non-detectable using current diagnostic tests.

Immunogen Preparation

Induction and interpretation of a humoral immune response directed against gp41 structural epitopes requires both immunogen preparation and antibody characterization. Synthetic peptides and recombinant proteins can both be used to generate antigenic structures corresponding to gp41 fusion active domains.

In one aspect of the invention, target immunogens model the heptad repeat region delineated by the P-17 peptide (capable of forming a trimeric coiled-coil structure). In another aspect of the invention, target immunogens model the transmembrane-proximal amphipathic α-helical segment delineated by the P-18 peptide. This region in the absence of the coiled-coil core exhibits random coil solution structure. (Wild, C., et al., *Proc. Natl. Acad. Sci. USA* 89:10537-10541 (1992); Wild, C., et al., *AIDS Res. Hum. Retroviruses* 9:1051-1053 (1993); Wild, C., et al., *Proc. Natl. Acad. Sci. USA* 91:9770-9774 (1994)). In another aspect, combinations of these target immnunogens are employed for raising antibodies.

In another aspect of the invention the target immunogen is the six helix hydrophobic bundle. This bundle is formed by the specific association of these two distal regions of the ectodomain of gp41 (Chan, D. C., et al, *Cell* 89:263-273 (1997); Lu, M., et al., *Nature Struct. Biol.* 2:1075-1082 (1995)). These constructs will mimic entry determinants which form and function during HIV-1 entry.

Synthetic Methods of Immunogen Preparation

Immunogens can be prepared by several different routes. The constructs can be generated from synthetic peptides. This involves preparing each sequence as a peptide monomer followed by post-synthetic modifications to generate the appropriate oligomeric structures. The peptides are synthesized by standard solid-phase methodology. To generate a trimeric coiled-coil structure, the P-17 peptide monomer is solubilized under conditions which favor oligomerization. These conditions include a 20 mM phosphate buffer, pH 4.5 and a peptide concentration of 100 μM (Wild, C., et al., *Proc. Natl. Acad. Sci. USA* 89:10537-10541 (1992)). The structure which forms under these conditions can be optionally stabilized by chemical crosslinking, for example using gluteraldehyde.

Figure 2:
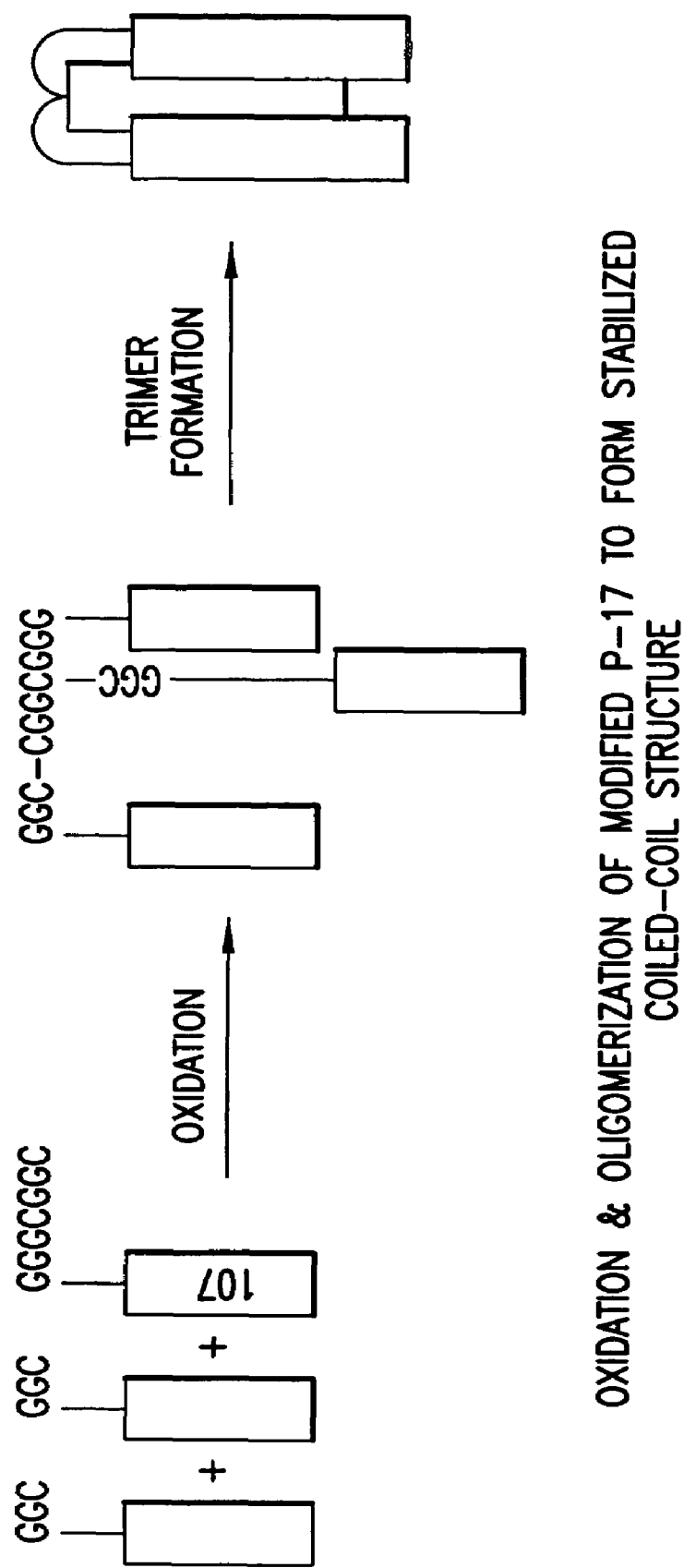
FIG. 2 illustrates the formation of multimeric peptide constructs corresponding to the heptad repeat region of gp41 (represented by P-17) and one or more suitable linker peptides.

Alternatively, a protocol which makes use of intermolecular disulfide bond formation to stabilize the trimeric coiled-coil structure can be employed in order to avoid any disruptive effect the cross-linking process might have on the structural components of this construct. This approach uses the oxidation of appropriately positioned cysteine residues within the peptide sequence to stabilize the oligomeric structure. This requires the addition of a short linker sequence to the N terminus of the P-17 peptide. The trimeric coiled-coil structure which is formed by this approach will be stabilized by the interaction of the cysteine residues (FIG. 2). The trimer is separated from higher order oligomeric forms, as well as residual monomer, by size exclusion chromatography and characterized by analytical ultracentrifugation. These covalently stabilized coiled-coil oligomers serve as the core structure for preparation of a six helix bundle.

To accomplish preparation of a six helix bundle, an excess of P-18 peptide is added to the purified core structure. After incubation the reaction mixture is subjected to a cross-linking procedure to stabilize the higher order products of the specific association of these two peptides. The desired material is isolated by size exclusion chromatography and characterized by analytical ultracentrifugation. The immunogen corresponding only to the P-18 peptide requires no specific post-synthetic modifications. Using this approach, three separate target constructs are generated rapidly and in large amounts.

Recombinant Methods of Immunogen Preparation

Another method for preparing target immunogens involves the use of a bacterial expression vector to generate recombinant gp41 fragments. The use of an expression vector to produce the peptides and polypeptides capable of forming the entry-relevant immunogens of the present invention adds a level of versatility to immunogen preparation.

New and modified forms of the antigenic targets are contemplated as the structural determinants of HIV-1 entry are better understood. The recombinant approach readily accommodates these changes. Also, this method of preparation allows for the ready modification of the various constructs (i.e. the addition of T- or B-cell epitopes to the recombinant gp41 fragments to increase immunogenicity). In addition, a form of the six helix hydrophobic core structure is generated which will not require additional stabilization, since determining the antigenic nature of this structure is important. Finally, these recombinant constructs can be employed as a tool to provide valuable insights into additional structural components which form and function in gp41 during the process of virus entry.

Thus, as part of the invention, novel fusion polypeptides (conjugates) are also provided, as are vectors, host cells and recombinant methods for producing the same. The present invention provides isolated nucleic acid molecules comprising a polynucleotide encoding the conjugates of the invention.

The present invention also relates to recombinant vectors, which include the isolated nucleic acid molecules of the present invention, and to host cells containing the recombinant vectors, as well as to methods of making such vectors and host cells and for using them for production of fusion polypeptides or peptides by recombinant techniques.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as that described herein. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in E. coli and other bacteria. Representative examples of appropriate hosts include, but are not limited to, bacterial cells, such as E. coli, Streptomyces and Salmonella typhimurium cells; fungal cells, such as yeast cells; insect cells such as Drosophila S2 and Spodoptera Sf9 cells; animal cells such as CHO, COS and Bowes melanoma cells; and plant cells. Appropriate culture mediums and conditions for the above-described host cells are known in the art.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., Basic Methods In Molecular Biology (1986).

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art.

The fusion protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

A bacterial expression vector (kindly provided by Dr. Terrance Oas, Duke University) was developed specifically for the expression of small proteins. This plasmid, pTCLE-G2C, is based on pAED4, a T7 expression vector. A modified TrpLE (Yansura, D. G., Methods Enzymol. 185:161-166 (1990)) fusion peptide (provided by Dr. Peter Kim) was inserted after the T7 promoter (Studier, F. W., et al., Methods Enzymol. 185:60-89 (1990)). There is an in frame Nde I site at the end of the TrpLE peptide that encodes a methionine cyanogen bromide (CNBr) cleavage site. This vector was used in an earlier study to express a recombinant form of the P-17 peptide (Calderone, T. L., et al., J. Mol. Biol. 262: 407412 (1996)) and has been modified to expresses the P-18 peptide.

To generate a six helix hydrophobic core structure, several combinations of the heptad repeat (for example, P-17 or P-15) region and the amphipathic α-helical (for example, P-16 or P-18) segment of gp41 are separated by a flexible linker of amino acid residues. For example, (GGGGS)$_3$ (SEQ ID NO:7) can be encoded into the vector. This is accomplished by standard PCR methods. The (GGGGS)$_3$ (SEQ ID NO:7) linker motif is encoded by a synthetic oligonucleotide which is ligated between the P-17 and P-18 encoding regions of the expression vector.

All constructions are characterized by multiple restriction enzyme digests and sequencing. The success of this approach to attain multicomponent interactions has been recently demonstrated (Huang, B., et al., J. Immunol. 158: 216-225 (1997)).

Examples of the novel constructs or conjugates that can be formed by the method are described above.

Figure 3:
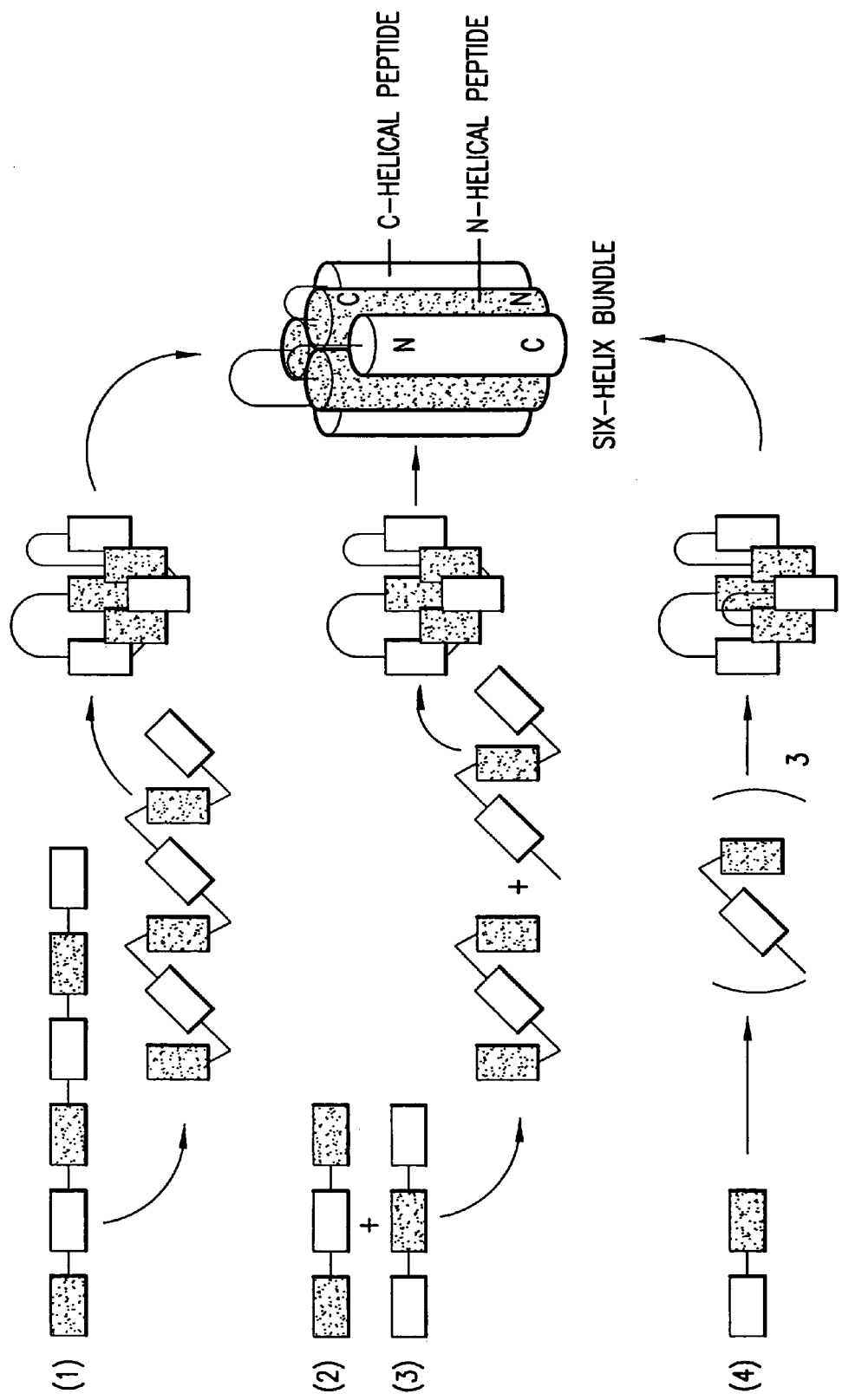
FIG. 3 illustrates the construction of conjugates of the invention derived from repeating gp41 fragments; and their subsequent folding and interaction to form immunologically relevant epitopes.

Based on the parallel orientation of the subunits of the coiled coil core and the antiparallel orientation of the amphipathic α-helical segment in the six helix bundle, these constructs fold to generate the desired structures (See, FIG. 3.). Following expression, the recombinant gp41 fragments are isolated as inclusion bodies, cleaved from the leader sequence by cyanogen bromide, and separated from the leader by-product by size exclusion chromatography step (SUPERDEX 75). This protocol has been successfully used in the purification of large quantities of a modified form of the P-17 peptide (Calderone, T. L., et al., J. Mol. Biol. 262:407-412 (1996)). Recombinant constructs (2) and (3) are mixed in equal molar quantities under non-denaturing conditions to generate a six-helix hydrophobic core structure. Constructs (1) and (4) will fold either intra- or intermolecularly to generate the same or similar structures (see FIG. 3 for the folding process). The desired product is purified by size exclusion chromatography on a SUPERDEX 75 FPLC column and characterized by molecular weight under using a Beckman Model XL-A analytical ultracentrifuge.

Definitions

The phrase "entry-relevant" as employed herein, refers to particular molecular conformations or structures that occur or are exposed following interaction of HIV with the cell surface during viral entry, and the role of particular amino acid sequences and molecular conformations or structures in viral entry.

The term "neutralizing" as employed herein refers to the ability to inhibit entry of HIV into cells, including an amount of inhibition that is useful for reducing or preventing infection of uninfected cells by the virus.

The term "HIV" as used herein refers to all strains and isolates of human immunodeficiency virus type 1. The constructs of the invention were based upon HIV-1 gp41, and the numbering of amino acids in HIV proteins and fragments thereof given herein is with respect to the HIV-$1_{LAI}$ isolate. However, it is to be understood, that while HIV-1 viral infection and the effects of the present invention on such HIV-1 infection are being used herein as a model system, the entry mechanism that is being targeted is relevant to all strains and isolates of HIV-1. Hence the invention is directed to "broadly neutralizing" methods.

The phrase "heptad repeat" or "heptad repeat region" as employed herein, refers to a common protein motif having a 4-3 repeat of amino acids, commonly leucine and/or isoleucine, and is often associated with alpha-helical secondary structure. The "heptad repeat" can be represented by the following sequence:

$$-AA_1-AA_2-AA_3-AA_4-AA_5-AA_6-AA_7-$$

where $AA_1$ and $AA_4$ are each one of leucine or isoleucine; while $AA_2$, $AA_3$, $AA_5$, $AA_6$, and $AA_7$ can be any amino acid. See, Wild, C., et al., Proc. Natl. Acad. Sci. USA 89:10537-10541 (1992).

Peptides are defined herein as organic compounds comprising two or more amino acids covalently joined by peptide bonds. Peptides may be referred to with respect to the number of constituent amino acids, i.e., a dipeptide contains two amino acid residues, a tripeptide contains three, etc. Peptides containing ten or fewer amino acids may be referred to as oligopeptides, while those with more than ten amino acid residues are polypeptides.

Peptides

The complete gp41 amino acid sequence (HIV-1 Group M: Subtype B Isolate: LAI, N to C termini) is:

```
AVGIGALFLGFLGAAGSTMGARSMTLTVQARQLLSGIVQQQNNLLRAIEA      (SEQ ID NO:8)
QQHLLQLTVWGIKQLQARILAVERYLKDQQLLGIWGCSGKLICTTAVPWNAS
WSNKSLEQIWNNMTWMEWDREINNYTSLIHSLIEESQNQQEK
NEQELLELDKWASLWNWFNITNWLWYIKIFIMIVGGLVGLRIVFAVLSIV
NRVRQGYSPLSFQTHLP-TPRG-PDRPEGIEEEGGERDRDRSIRLVNGSL
ALIWDDLRSLCLFSYHRLRDLLLIVTRIVELLGRRGWEALKYWW
NLLQYWSQELKNSAVSLLNATAIAVAEGTDRVIEVVQGACRAIRHIPRRIRQG
LERILL.
```

N-terminal helix region:

```
ARQLLSGIVQQQNNLLRAIEAQQHLLQLTVWGIKQLQARILAVERYLKDQQLLGI  (SEQ ID NO:1)
```

Shown below is the sequence for residues 558-595 (SEQ ID NO:7) of the HIV-1$_{LAI}$ gp41 protein in the N-helical domain of the protein. The a and d subscripts denote the 4-3 positions of the heptad repeat.

```
N N L L R A I E A Q Q H L L Q L T V W G I K Q L Q A R I L A V E R Y L K D Q   (SEQ ID NO:2)
    d     a     d     a     d     a     d     a     d     a
              571             578             585
```

C-terminal helix region:

```
WNNMTWMEWDREINNYTSLIHSLIEESQNQQEKNEQELLELDKWASLWNWFNITNW   (SEQ ID NO:4)
                                                   50
```

Shown below is the amino acid sequence for residues 643-678 of the HIV-1$_{LAI}$ gp41 protein in the C-helical domain of the protein.

```
Y T S L I H S L I E E S Q N Q Q E K N E Q E L L E L D K W A S L W N W F   (SEQ ID NO:5)
    d     a     d     a     d     a     d     a     d     a
        647         654         661
```

Unlike the N-helix, when modeled as a peptide, the C-helical region of gp41 is not structured. However, when mixed with the N-peptide, the C-peptide does takes on α-helical structure as part of the core structure complex. The structure forms in vitro on mixing the peptides and can be characterized spectrophotometrically (Lu, M., et al., *Nat. Struct. Biol.* 2:1075-1082 (1995)). The initial determination of the effect of the mutations on C-helix structure may be performed by analyzing the ability of the mutant C-peptide to interact with the N-peptide and form the six-helix bundle. This analysis maybe carried out using circular dichroism. N-helical and C-helical domain peptides can be constructed from multiple strains of HIV, and can include deletions, insertions and substitutions that do not destroy the ability of the resulting peptide to elicit antibodies when employed alone or in combination with other peptides of the invention.

Examples of N-helical Domain Peptide Sequences (All sequences are listed from N-terminus to C-terminus.) from different HIV strains include, but are not limited to the following peptides:

HIV-1 Group M: Subtype B Isolate: LAI

```
     ARQLLSGIVQQQNNLLRAIEAQQHLLQLTVWGIKQLQARILAVERYLKDQQLLGI  (SEQ ID NO:1)
     SGIVQQQNNLLRAIEAQQHLLQLTVWGIKQLQARILAVERYLKDQ            (SEQ ID NO:9)
P15  SGIVQQQNNLLRAIEAQQHLLQLTVWGIKQLQARIL                     (SEQ ID NO:3)
P-17 NNLLRAIEAQQHLLQLTVWGIKQLQARILAVERYLKDQ                   (SEQ ID NO:2)
```

Subtype B Isolate: ADA

```
SGIVQQQNNLLRAIEAQQHLLQLTVWGIKQLQARVLALERYLRDQ  (SEQ ID NO:10)
SGIVQQQNNLLRAIEAQQHLLQLTVWGIKQLQARVL           (SEQ ID NO:11)
NNLLRAIEAQQHLLQLTVWGIKQLQARVLALERYLRDQ         (SEQ ID NO:12)
```

Subtype B Isolate: JRFL

```
SGIVQQQNNLLRAIEAQQRMLQLTVWGIKQLQARVLAVERYLGDQ  (SEQ ID NO:13)
SGIVQQQNNLLRAIEAQQRMLQLTVWGIKQLQARVL           (SEQ ID NO:14)
NNLLRAIEAQQRMLQLTVWGIKQLQARVLAVERYLGDQ         (SEQ ID NO:15)
```

Subtype B Isolate: 89.6

```
SGIVQQQNNLLRAIEAQQHMLQLTVWGIKQLQARVLALERYLRDQ  (SEQ ID NO:16)
SGIVQQQNNLLRAIEAQQHMLQLTVWGIKQLQARVL           (SEQ ID NO:17)
NNLLRAIEAQQHMLQLTVWGIKQLQARVLALERYLRDQ         (SEQ ID NO:18)
```

Subtype C Isolate: BU910812

```
SGIVQQQSNLLRAIEAQQHMLQLTVWGIKQLQARVLAIERYLRDQ  (SEQ ID NO:19)
SGIVQQQSNLLRAIEAQQHMLQLTVWGIKQLQARVL           (SEQ ID NO:20)
SNLLRAIEAQQHMLQLTVWGIKQLQARVLAIERYLRDQ         (SEQ ID NO:21)
```

Subtype D Isolate: 92UG024D

```
SGIVQQQNNLLRAIEAQQHLLQLTVWGLKQLQARVLAVESYLKDQ  (SEQ ID NO:22)
SGIVQQQNNLLRAIEAQQHLLQLTVWGLKQLQARVL           (SEQ ID NO:11)
NNLLRAIEAQQHLLQLTVWGIKQLQARVLAVESYLKDQ         (SEQ ID NO:23)
```

Subtype F Isolate: BZ163A

```
SGIVQQQSNLLRAIEAQQHLLQLTVWGIKQLQARVLAVERYLQDQ  (SEQ ID NO:24)
SGIVQQQSNLLRAIEAQQHLLQLTVWGIKQLQARVL           (SEQ ID NO:25)
SNLLRAIEAQQHLLQLTVWGIKQLQARVLAVERYLQDQ         (SEQ ID NO:26)
```

Subtype G Isolate: FI.HH8793

```
SGIVQQQSNLLRAIEAQQHLLQLTVWGIKQLQARVLALERYLRDQ    (SEQ ID NO:27)
SGIVQQQSNLLRAIEAQQHLLQLTVWGIKQLQARVL            (SEQ ID NO:25)
SNLLRAIEAQQHLLQLTVWGIKQLQARVLALERYLRDQ          (SEQ ID NO:28)
```

Subtype H Isolate: BE.VI997

```
SGIVQQQSNLLRAIQAQQHMLQLTVWGVKQLQARVLAVERYLKDQ    (SEQ ID NO:29)
SGIVQQQSNLLRAIQAQQHMLQLTVWGVKQLQARVL            (SEQ ID NO:30)
SNLLRAIQAQQHMLQLTVWGVKQLQARVLAVERYLKDQ          (SEQ ID NO:31)
```

Subtype J Isolate: SE.SE92809

```
SGIVQQQSNLLKAIEAQQHLLKLTVWGIKQLQARVLAVERYLKDQ    (SEQ ID NO:32)
SGIVQQQSNLLKAIEAQQHLLKLTVWGIKQLQARVL            (SEQ ID NO:33)
SNLLKAIEAQQHLLKLTVWGIKQLQARVLAVERYLKDQ          (SEQ ID NO:34)
```

Group N Isolate: CM.YBF30

```
SGIVQQQNILLRAIEAQQHLLQLSIWGIKQLQAKVLAIERYLRDQ    (SEQ ID NO:35)
SGIVQQQNILLRAIEAQQHLLQLSIWGIKQLQAKVL            (SEQ ID NO:36)
NILLRAIEAQQHLLQLSIWGIKQLQAKVLAIERYLRDQ          (SEQ ID NO:37)
```

Group O Isolate: CM.AN17OC

```
KGIVQQQDNLLRAIQAQQQLLRLSxWGIRQLRARLLALETLLQNQ    (SEQ ID NO:38)
KGIVQQQDNLLRAIQAQQQLLRLSxWGIRQLRARL             (SEQ ID NO:39)
DNLLRAIQAQQQLLRLSxWGIRQLRARLLALETLLQNQ          (SEQ ID NO:40)
```

Examples of C-helical Domain Peptide Sequences (All sequences are listed from N-terminus to C-terminus.) from different HIV strains include, but are not limited to the following peptides:

HIV-1 Group M: Subtype B Isolate: LAI

```
      WNNMTWMEWDREINNYTSLIHSLIEESQNQQEKNEQELLELDKWASLWNWFNITNW    (SEQ ID NO:4)
      WMEWDREINNYTSLIHSLIEESQNQQEKNEQELLELDKWASLWNWF              (SEQ ID NO:41)
P16   WMEWDREINNYTSLIHSLIEESQNQQEKNEQELL                          (SEQ ID NO:6)
P-18  YTSLIHSLIEESQNQQEKNEQELLELDKWASLWNWF                        (SEQ ID NO:5)
```

Subtype B Isolate: ADA

```
WMEWEREIENYTGLIYTLIEESQNQQEKNEQDLLALDKWASLWNWF    (SEQ ID NO:42)
WMEWEREIENYTGLIYTLIEESQNQQEKNEQDLL               (SEQ ID NO:43)
YTGLIYTLIEESQNQQEKNEQDLLALDKWASLWNWF             (SEQ ID NO:44)
```

Subtype B Isolate: JRFL

```
WMEWEREIDNYTSEIYTLIEESQNQQEKNEQELLELDKWASLWNWF    (SEQ ID NO:45)
WMEWEREIDNYTSEIYTLIEESQNQQEKNEQELL                (SEQ ID NO:46)
YTSEIYTLIEESQNQQEKNEQELLELDKWASLWNWF              (SEQ ID NO:47)
```

Subtype B Isolate: 89.6

```
WMEWEREIDNYTDYIYDLLEKSQTQQEKNEKELLELDKWASLWNWF    (SEQ ID NO:48)
WMEWEREIDNYTDYIYDLLEKSQTQQEKNEKELL                (SEQ ID NO:49)
YTDYIYDLLEKSQTQQEKNEKELLELDKWASLWNWF              (SEQ ID NO:50)
```

Subtype C Isolate: BU910812

```
WIQWDREISNYTGIIYRLLEESQNQQENNEKDLLALDKWQNLWSWF    (SEQ ID NO:51)
WIQWDREISNYTGIIYRLLEESQNQQENNEKDLL                (SEQ ID NO:52)
YTGIIYRLLEESQNQQENNEKDLLALDKWQNLWSWF              (SEQ ID NO:53)
```

Subtype D Isolate: 92UG024D

```
WMEWEREISNYTGLIYDLIEESQIQQEKNEKDLLELDKWASLWNWF    (SEQ ID NO:54)
WMEWEREISNYTGLIYDLIEESQIQQEKNEKDLL                (SEQ ID NO:55)
YTGLIYDLIEESQIQQEKNEKDLLELDKWASLWNWF              (SEQ ID NO:56)
```

Subtype F Isolate: BZ163A

```
WMEWQKEISNYSNEVYRLIEKSQNQQEKNEQGLLAL              (SEQ ID NO:57)
DKWASLWNWF
WMEWQKEISNYSNEVYRLIEKSQNQQEKNEQGLL                (SEQ ID NO:58)
YSNEVYRLIEKSQNQQEKNEQGLLALDKWASLWNWF              (SEQ ID NO:59)
```

Subtype G Isolate: FI.HH8793

```
WIQWDREISNYTQQIYSLIEESQNQQEKNEQDLLAL              (SEQ ID NO:60)
DNWASLWTWF
WIQWDREISNYTQQIYSLIEESQNQQEKNEQDLL                (SEQ ID NO:61)
YTQQIYSLIEESQNQQEKNEQDLLALDNWASLWTWF              (SEQ ID NO:62)
```

Subtype H Isolate: BE.VI997

```
WMEWDRQIDNYTEVIYRLLELSQTQQEQNEQDLLAL              (SEQ ID NO:63)
DKWDSLWNWF
WMEWDRQIDNYTEVIYRLLELSQTQQEQNEQDLL                (SEQ ID NO:64)
YTEVLYRLLELSQTQQEQNEQDLLALDKWDSLWNWF              (SEQ ID NO:65)
```

Subtype J Isolate: SE.SE92809

```
WIQWEREINNYTGIIYSLIEEAQNQQENNEKDLLAL              (SEQ ID NO:66)
DKWTNLWNWFN
WIQWEREINNYTGIIYSLIEEAQNQQENNEKDLL                (SEQ ID NO:67)
YTGIIYSLIIEEAQNQQENNEKDLLALDKWTNLWNW              (SEQ ID NO:68)
FN
```

Group N Isolate: CM.YBF30

```
WQQWDEKVRNYSGVIFGLLEQAQEQQNTNEKSLLEL              (SEQ ID NO:69)
DQWDSLWSWF
WQQWDEKVRNYSGVIFGLIEQAQEQQNTNEKSLL                (SEQ ID NO:70)
YSGVIFGLLEQAQEQQNTNEKSLLELDQWDSLWSWF              (SEQ ID NO:71)
```

Group O Isolate: CM.ANT70C

```
WQEWDRQISNISSTIYEEIQKAQVQQEQNEKKLLEL              (SEQ ID NO:72)
DEWASIWNWL
WQEWDRQISNISSTIYEEIQKAQVQQEQNEKKLL                (SEQ ID NO:73)
ISSTIYEEIQKAQVQQEQNEKKLLELDEWASIWNWL              (SEQ ID NO:74)
```

The peptides and conjugates of the present invention may be acylated at the NH₂ terminus, and may be amidated at the COOH terminus.

The peptides and conjugates of the invention may include conservative amino acid substitutions. Conserved amino acid substitutions consist of replacing one or more amino acids of the peptide sequence with amino acids of similar charge, size, and/or hydrophobicity characteristics, such as, for example, a glutamic acid (E) to aspartic acid (D) amino acid substitution. When only conserved substitutions are made, the resulting peptide is functionally equivalent to the peptide from which it is derived.

Peptide sequences defined herein are represented by one-letter symbols for amino acid residues as follows:

| A | alanine | L | leucine |
|---|---|---|---|
| R | arginine | K | lysine |
| N | asparagine | M | methionine |
| D | aspartic acid | F | phenylalamine |
| C | cysteine | P | proline |
| Q | glutamine | S | serine |
| E | glutamic acid | T | threonine |
| G | glycine | W | tryptophan |
| H | histidine | Y | tyrosine |
| I | isoleucine | V | valine |

The peptides and conjugates of the invention may include amino acid insertions which consist of single amino acid residues or stretches of residues ranging from 2 to 15 amino acids in length. One or more insertions may be introduced into the peptide, peptide fragment, analog and/or homolog.

The peptides and conjugates of the invention may include amino acid deletions of the full length peptide, analog, and/or homolog. Such deletions consist of the removal of one or more amino acids from the full-length peptide sequence, with the lower limit length of the resulting peptide sequence being 4 to 6 amino acids. Such deletions may involve a single contiguous portion or greater than one discrete portion of the peptide sequences.

The peptides of the invention may be synthesized or prepared by techniques well known in the art. See, for example, Creighton, *Proteins: Structures and Molecular Principles*, W. H. Freeman & Co., New York, N.Y. (1983), which is incorporated herein by reference in its entirety. Short peptides, for example, can be synthesized as a solid support or in solution. Longer peptides may be made using recombinant DNA techniques. Here, the nucleotide sequences encoding the peptides of the invention may be synthesized, and/or cloned, and expressed according to techniques well known to those of ordinary skill in the art. See, for example, Sambrook, et al., *Molecular Cloning, A Laboratory Manual*, Vols. 1-3, Cold Spring Harbor Press, Cold Spring Harbor, N.Y. (1989).

In yet another embodiment of the invention, peptides comprising the sequences described above may be synthesized with additional chemical groups present at their amino and/or carboxy termini, such that, for example, the stability, bioavailability, and/or immunogenic activity of the peptides is enhanced. For example, hydrophobic groups such as carbobenzoxy, dansyl, or t-butyloxycarbonyl groups, may be added to the peptides' amino termini. Likewise, an acetyl group or a 9-fluorenylmethoxy-carbonyl group may be placed at the peptides' amino termini. Additionally, the hydrophobic group t-butyloxycarbonyl, or an amido group may be added to the peptides' carboxy termini. In one preferred embodiment, carrier proteins, such as keyhole limpet hemocyanin, ovalbumin, BSA or tetanus toxoid are added to the peptide.

With reference to the peptides P-17 and P-18, deletion mutants are further described.

The peptide P-18 corresponds to amino acid residues 638 to 673 of the transmembrane protein gp41 from the HIV-1$_{LAI}$ isolate:

In addition to the full-length C-helical peptides identified above, useful peptides of the invention may include truncations of the C-helical peptides (SEQ ID NO:4) which exhibit the ability to raise neutralizing antibodies or form a six-helix hydrophobic core structure under conditions described herein. Such truncated peptides may comprise peptides of between 3 and 56 amino acid residues, i.e., peptides ranging in size from a tripeptide to a 56-mer polypeptide. As an example, such peptides are listed for P-18 in Tables I and II, below. Peptide sequences in these tables are listed from amino (left) to carboxy (right) terminus. "X" may represent an amino group (—NH₂) and "Z" may represent a carboxyl (—COOH) group. Alternatively, as described below, "X" and/or "Z" may represent a hydrophobic group, an acetyl group, a FMOC group, an amido group, or a covalently attached macromolecule.

TABLE I

| Carboxy Truncations of SEQ ID NO:5 |
|---|
| X-YTS-Z |
| X-YTSL-Z |
| X-YTSLI-Z |
| X-YTSLIH-Z |
| X-YTSLIHS-Z |
| X-YTSLIHSL-Z |
| X-YTSLIHSLI-Z |
| X-YTSLIHSLIE-Z |
| X-YTSLIHSLIEE-Z |
| X-YTSLIHSLIEES-Z |
| X-YTSLIHSLIEESQ-Z |
| X-YTSLIHSLIEESQN-Z |
| X-YTSLIHSLIEESQNQ-Z |
| X-YTSLIHSLIEESQNQQ-Z |
| X-YTSLIHSLIEESQNQQE-Z |
| X-YTSLIHSLIEESQNQQEK-Z |
| X-YTSLIHSLIEESQNQQEKN-Z |
| X-YTSLIHSLIEESQNQQEKNE-Z |
| X-YTSLIHSLIEESQNQQEKNEQ-Z |
| X-YTSLIHSLIEESQNQQEKNEQE-Z |
| X-YTSLIHSLIEESQNQQEKNEQEL-Z |
| X-YTSLIHSLIEESQNQQEKNEQELL-Z |
| X-YTSLIHSLIEESQNQQEKNEQELLE-Z |
| X-YTSLIHSLIEESQNQQEKNEQELLEL-Z |

TABLE I-continued
Carboxy Truncations of SEQ ID NO:5

X-YTSLIHSLIEESQNQQEKNEQELLELD-Z

X-YTSLIHSLIEESQNQQEKNEQELLELDK-Z

X-YTSLIHSLIEESQNQQEKNEQELLELDKW-Z

X-YTSLIHSLIEESQNQQEKNEQELLELDKWA-Z

X-YTSLIHSLIEESQNQQEKNEQELLELDKWAS-Z

X-YTSLIHSLIEESQNQQEKNEQELLELDKWASL-Z

X-YTSLIHSLIEESQNQQEKNEQELLELDKWASLW-Z

X-YTSLIHSLIEESQNQQEKNEQELLELDKWASLWN-Z

X-YTSLIHSLIEESQNQQEKNEQELLELDKWASLWNW-Z

X-YTSLIHSLIEESQNQQEKNEQELLELDKWASLWNWF-Z

The one letter amino acid code is used.
"X" may represent a hydrogen attached to the terminal amino group, an amino protecting group including, but not limited to, carbobenzoxyl, dansyl, or t-butyloxycarbonyl; an acetyl group; a 9-fluorenyl-methoxy-carbonyl (FMOC) group; a macromolecular carrier group including, but not limited to, lipid-fatty acid conjugates, polyethylene glycol, or carbohydrates.
"Z" may represent a terminal carboxyl (COOH); an amido group; an ester group (COOR) including, but not limited to, a t-butyloxycarbonyl group; a macromolecular carrier group including, but not limited to, lipid-fatty acid conjugates, polyethylene glycol, or carbohydrates.

TABLE II
Amino Truncations of SEQ ID NO:5

X-NWF-Z

X-WNWF-Z

X-LWNWF-Z

X-SLWNWF-Z

X-ASLWNWF-Z

X-WASLWNWF-Z

X-KWASLWNWF-Z

X-DKWASLWNWF-Z

X-LDKWASLWNWF-Z

X-ELDKWASLWNWF-Z

X-LELDKWASLWNWF-Z

X-LLELDKWASLWNWF-Z

X-ELLELDKWASLWNWF-Z

X-QELLELDKWASLWNWF-Z

X-EQELLELDKWASLWNWF-Z

X-NEQELLELDKWASLWNWF-Z

X-KNEQELLELDKWASLWNWF-Z

X-EKNEQELLELDKWASLWNWF-Z

TABLE II-continued
Amino Truncations of SEQ ID NO:5

X-QEKNEQELLELDKWASLWNWF-Z

X-QQEKNEQELLELDKWASLWNWF-Z

X-NQQEKNEQELLELDKWASLWNWF-Z

X-QNQQEKNEQELLELDKWASLWNWF-Z

X-SQNQQEKNEQELLELDKWASLWNWF-Z

X-ESQNQQEKNEQELLELDKWASLWNWF-Z

X-EESQNQQEKNEQELLELDKWASLWNWF-Z

X-IEESQNQQEKNEQELLELDKWASLWNWF-Z

X-LIEESQNQQEKNEQELLELDKWASLWNWF-Z

X-SLIEESQNQQEKNEQELLELDKWASLWNWF-Z

X-HSLIEESQNQQEKNEQELLELDKWASLWNWF-Z

X-IHSLIEESQNQQEKNEQELLELDKWASLWNWF-Z

X-LIHSLIEESQNQQEKNEQELLELDKWASLWNWF-Z

X-SLIHSLIEESQNQQEKNEQELLELDKWASLWNWF-Z

X-TSLIHSLIEESQNQQEKNEQELLELDKWASLWNWF-Z

X-YTSLIHSLIEESQNQQEKNEQELLELDKWASLWNWF-Z

The one letter amino acid code is used.
"X" may represent a hydrogen attached to the terminal amino group, an amino protecting group including, but not limited to, carbobenzoxyl, dansyl, or t-butyloxycarbonyl; an acetyl group; a 9-fluorenylmethoxy-carbonyl (FMOC) group; a macromolecular carrier group including, but not limited to, lipid-fatty acid conjugates, polyethylene glycol, or carbohydrates.
"Z" may represent a terminal carboxyl (COOH); an amido group; an ester group (COOR) including, but not limited to, a t-butyloxycarbonyl group; a macromolecular carrier group including, but not limited to, lipid-fatty acid conjugates, polyethylene glycol, or carbohydrates.

The peptides also include analogs of which may include, but are not limited to, peptides comprising the a full-length or truncated sequence, containing one or more amino acid substitutions, insertions and/or deletions.

There exists a striking amino acid conservation within the C-helical regions of HIV-1 and HIV-2. The amino acid conservation is of a periodic nature, suggesting some conservation of structure and/or function. A useful peptide derived from the HIV-2$_{NHZ}$ isolate has the 36 amino acid sequence (reading from amino to carboxy terminus):

NH$_2$-LEANISQSLEQAQIQQEKNMYELQKLNSWDVFT (SEQ ID NO:5)
NWL-COOH

Further, peptides useful for forming "entry-relevant" structures include peptides corresponding to the N-helical domain of gp41. One example of such a peptide, P-17, corresponds to residues 558 to 595 of the transmembrane protein gp41 from the HIV-$1_{LAI}$ isolate.

In addition to the full-length N-helical peptides (for example, (SEQ D NO:1)) shown above, the peptides may include truncations of these peptides which exhibit the ability to form stable coiled-coil structure. Such truncated peptides may comprise peptides of between 3 and 55 amino acid residues, i.e., peptides ranging in size from a tripeptide to a 55-mer polypeptide, as shown in Tables III and IV, below for P-17. Peptide sequences in these tables are listed from amino (left) to carboxy (right) terminus. "X" may represent an amino group (—NH$_2$) and "Z" may represent a carboxyl (—COOH) group. Alternatively, "X" and/or "Z" may represent a hydrophobic group, an acetyl group, a FMOC group, an amido group or a covalently attached macromolecular group.

TABLE III

Carboxy Truncations of SEQ ID NO:2

X-NNL-Z

X-NNLL-Z

X-NNLLR-Z

X-NNLLRA-Z

X-NNLLRAI-Z

X-NNLLRAIE-Z

X-NNLLRAIEA-Z

X-NNLLRAIEAQ-Z

X-NNLLRAIEAQQ-Z

X-NNLLRAIEAQQH-Z

X-NNLLRAIEAQQHL-Z

X-NNLLRAIEAQQHLL-Z

X-NNLLRAIEAQQHLLQ-Z

X-NNLLRAIEAQQHLLQL-Z

X-NNLLRAIEAQQHLLQLT-Z

X-NNLLRAIEAQQHLLQLTV-Z

X-NNLLRAIEAQQHLLQLTVW-Z

X-NNLLRAIEAQQHLLQLTVWQ-Z

X-NNLLRAIEAQQHLLQLTVWQI-Z

X-NNLLRAIEAQQHLLQLTVWQIK-Z

X-NNLLRAIEAQQHLLQLTVWQIKQ-Z

X-NNLLRAIEAQQHLLQLTVWQIKQL-Z

X-NNLLRAIEAQQHLLQLTVWQIKQLQ-Z

X-NNLLRAIEAQQHLLQLTVWQIKQLQA-Z

X-NNLLRAIEAQQHLLQLTVWQIKQLQAR-Z

X-NNLLRAIEAQQHLLQLTVWQIKQLQARI-Z

X-NNLLRAIEAQQHLLQLTVWQIKQLQARIL-Z

X-NNLLRAIEAQQHLLQLTVWQIKQLQARILA-Z

X-NNLLRAIEAQQHLLQLTVWQIKQLQARILAV-Z

X-NNLLRAIEAQQHLLQLTVWQIKQLQARILAVE-Z

TABLE III-continued

Carboxy Truncations of SEQ ID NO:2

X-NNLLRAIEAQQHLLQLTVWQIKQLQARILAVER-Z

X-NNLLRAIEAQQHLLQLTVWQIKQLQARILAVERY-Z

X-NNLLRAIEAQQHLLQLTVWQIKQLQARILAVERYL-Z

X-NNLLRAIEAQQHLLQLTVWQIKQLQARILAVERYLK-Z

X-NNLLRAIEAQQHLLQLTVWQIKQLQARILAVERYLKD-Z

X-NNLLRAIEAQQHLLQLTVWQIKQLQARILAVERYLKDQ-Z

The one letter amino acid code is used.
"X" may represent a hydrogen attached to the terminal amino group, an amino protecting group including, but not limited to, carbobenzoxyl, dansyl, or t-butyloxycarbonyl; an acetyl group; a 9-fluorenyl-methoxy-carbonyl (FMOC) group; a macromolecular carrier group including, but not limited to, lipid-fatty acid conjugates, polyethylene glycol, or carbohydrates.
"Z" may represent a terminal carboxyl (COOH); an amido group; an ester group (COOR) including, but not limited to, a t-butyloxycarbonyl group; a macromolecular carrier group including, but not limited to, lipid-fatty acid conjugates, polyethylene glycol, or carbohydrates.

TABLE IV

Amino Truncations of SEQ ID NO:2

X-KDQ-Z

X-LKDQ-Z

X-YLKDQ-Z

X-RYLKDQ-Z

X-ERYLKDQ-Z

X-VERYLKDQ-Z

X-AVERYLKDQ-Z

X-LAVERYLKDQ-Z

X-ILAVERYLKDQ-Z

X-RILAVERYLKDQ-Z

X-ARILAVERYLKDQ-Z

X-QARILAVERYLKDQ-Z

X-LQARILAVERYLKDQ-Z

X-QLQARILAVERYLKDQ-Z

X-KQLQARILAVERYLKDQ-Z

X-IKQLQARILAVERYLKDQ-Z

X-QIKQLQARILAVERYLKDQ-Z

X-WQIKQLQARILAVERYLKDQ-Z

X-VWQIKQLQARILAVERYLKDQ-Z

X-TVWQIKQLQARILAVERYLKDQ-Z

X-LTVWQIKQLQARILAVERYLKDQ-Z

X-QLTVWQIKQLQARILAVERYLKDQ-Z

TABLE IV-continued

Amino Truncations of SEQ ID NO:2

```
X-LQLTVWQIKQLQARILAVERYLKDQ-Z
X-LLQLTVWQIKQLQARILAVERYLKDQ-Z
X-HLLQLTVWQIKQLQARILAVERYLKDQ-Z
X-QHLLQLTVWQIKQLQARILAVERYLKDQ-Z
X-QQHLLQLTVWQIKQLQARILAVERYLKDQ-Z
X-AQQHLLQLTVWQIKQLQARILAVERYLKDQ-Z
X-EAQQHLLQLTVWQIKQLQARILAVERYLKDQ-Z
X-IEAQQHLLQLTVWQIKQLQARILAVERYLKDQ-Z
X-AIEAQQHLLQLTVWQIKQLQARILAVERYLKDQ-Z
X-RAIEAQQHLLQLTVWQIKQLQARILAVERYLKDQ-Z
X-LRAIEAQQHLLQLTVWQIKQLQARILAVERYLKDQ-Z
X-LLRAIEAQQHLLQLTVWQIKQLQARILAVERYLKDQ-Z
X-NLLRAIEAQQHLLQLTVWQIKQLQARILAVERYLKDQ-Z
X-NNLLRAIEAQQHLLQLTVWQIKQLQARILAVERYLKDQ-Z
```

The one letter amino acid code is used.
"X" may represent a hydrogen attached to the terminal amino group, an amino protecting group including, but not limited to, carbobenzoxyl, dansyl, or t-butyloxycarbonyl; an acetyl group; a 9-fluorenylmethoxy-carbonyl (FMOC) group; a macromolecular carrier group including, but not limited to, lipid-fatty acid conjugates, polyethylene glycol, or carbohydrates.
"Z" may represent a terminal carboxyl (COOH); an amido group; an ester group (COOR) including, but not limited to, a t-butyloxycarbonyl group; a macromolecular carrier group including, but not limited to, lipid-fatty acid conjugates, polyethylene glycol, or carbohydrates.

The N-helical peptides also include analogs and/or truncations which may include, but are not limited to, peptides comprising the full-length or a truncated sequence, containing one or more amino acid substitutions, insertions and/or deletions.

Antibody Generation and Characterization

Generation and characterization of the antibodies generated against novel gp41 epitopes constitutes the second aspect of the invention. The experimental sera and monoclonal antibodies generated against the target imnmunogens are subjected to thorough biophysical and biological evaluation.

Antibodies are generated following established protocols. All small animal work (immunizations, bleeds, and hybridoma production) is carried out by standard methods known to those of skill in the art. A first set of immunogens consists of the peptide constructs P-15 or P-17 (capable of forming trimeric coiled-coil multimers, optionally stabilized by chemical cross-linking or oxidation), P-16 or P-18, and the P-17/P-18 mixture or P-15/P-16 mixture (wherein the peptides are optionally chemically or oxidatively cross-linked). In one set of experiments, the immunogens are conjugated to a carrier such as KLH.

Balb-c mice are immunized with each of these constructs. Due to possible disruptive effects of carrier conjugation on antigen structure, one group of mice from each set can be immunized with 100 µg of unconjugated peptide, while another group of mice can receive 100 µg of antigen conjugated to KLH. Following the initial immunization the animals receive a 100 µg boost on day 14 followed by 50 µg boosts on days 30 and 45. Bleeds occur two weeks following the final boost. Mice are also immunized with the recombinant constructs following the same outline as that for the peptide immunogens.

Alternative immunization approaches include the use of a recombinant adenovirus vector expressing all or part of the HIV-1 envelope glycoprotein gp120/gp41 as the primary immunogen followed by booster immunizations with the gp41 peptides, proteins or other constructs.

The polyclonal sera generated by the immunization of experimental animals undergo an initial screen for virus inhibition. Antiviral activity is evaluated in both cell-cell fusion and neutralization assays. In this second format, a representative sample of lab adapted and primary virus isolates is used. Both assays are carried out according to protocols described previously (Wild, C., et al., *Proc. Natl. Acad. Sci. USA* 89:10537-10541 (1992); Wild, C., et al., *Proc. Natl. Acad. Sci. USA* 91:12676-12680 (1994); Wild, C., et al., *Proc. Natl. Acad. Sci. USA* 91:9770-9774 (1994)). Samples are also screened by ELISA to characterize binding. The antigen panel includes all experimental immunogens. Animals with sera samples which test positive for binding to one or more experimental immunogens are candidates for use in MAb production. Following this initial screen, one animal representing each experimental immunogen is selected for monoclonal antibody production. The criteria for this selection is based on neutralizing antibody titers and in the absence of neutralization, binding patterns against the panel of structured immunogens.

Hybridoma supernatants are screened by ELISA, against structured and non-structured peptides and recombinants. Samples that are ELISA negative or weakly positive are further characterized for IgG. If IgG is present the material is screened in the biophysical and biological assays. Strongly positive samples are screened for their ability to neutralize virus and bind envelope. The experimental material can be further tested against a panel representing the spectrum of HIV-1 isolates. These isolates include lab adapted and primary virus strains, syncytium and non-syncytium inducing isolates, virus representing various geographic subtypes, and viral isolates which make use of the range of second receptors during virus entry. These neutralization assays employ either primary cell and cell line targets as required.

Antibodies are characterized in detail for their ability to bind HIV envelope under various conditions. It is another object of the invention to determine the gp41 target epitopes are exposed on native envelope or if the envelope must first undergo some interaction which triggers a conformational change i.e binding CD4 and/or co-receptor in order to expose these epitopes. For detection of antibody binding to native envelope, immunoprecipitations on Env-expressing cells and virions, both intact and lysed are performed using non-ionic detergents (Furata, R A et al., *Nat. Struct. Biol.* 5(4):276-279 (1997); White, J. M. and I. A. Wilson, *J. Cell Biol.* 105:2887-2894 (1987); Kemble, G. W., et al., *J. Virol.* 66:4940-4950 (1992)). Antibody binding to cell lysates and intact virions are also assayed in an ELISA format. Flow cytometry experiments are performed to determine binding to envelope expressing cells. Cross-competition experiments using other mapped Mabs, human sera, and peptides can also be performed. To characterize "triggers" to the conformational change, antibody binding to virus in the presence and absence of both sCD4 and target cells can be compared (White, J. M. and I. A. Wilson, *J. Cell Biol.* 105:2887-2894 (1987); Kemble, G. W., et al., *J. Virol.* 66:4940-4950 (1992)). Because the gp41 regions are highly conserved, epitope exposure using several different envelopes can be compared to discern possible differences in structure between primary, lab-adapted and genetically diverse virus isolates.

Pharmaceutical Compositions and Methods of Using

The immunogenic constructs of the present invention can be employed in vaccines in an amount effective depending on the route of administration. Although subcutaneous or intramuscular routes of administration are preferred, peptides, multimers or peptide conjugates of the present invention can also be administered by an intraperitoneal or intravenous route. One skilled in the art will appreciate that the amounts to be administered for any particular treatment protocol can be readily determined without undue experimentation.

The vaccines of the present invention may be employed in such forms as capsules, liquid solutions, suspensions or elixirs for oral administration, or sterile liquid forms such as solutions or suspensions. Any inert carrier is preferably used, such as saline, phosphate-buffered saline, or any such carrier in which the conjugate vaccine has suitable solubility properties. The vaccines may be in the form of single dose preparations or in multi-dose flasks which can be used for mass vaccination programs. Reference is made to Remington's *Pharmaceutical Sciences*, Osol, ed., Mack Publishing Co., Easton, Pa. (1980), and *New Trends and Developments in Vaccines*, Voller, et al., eds., University Park Press, Baltimore, Md. (1978), for methods of preparing and using vaccines.

The vaccines of the present invention may further comprise adjuvants which enhance production of HIV-specific antibodies. Such adjuvants include, but are not limited to, various oil formulations such as Freund's complete adjuvant (CFA), stearyl tyrosine (ST, see U.S. Pat. No. 4,258,029), the dipeptide known as MDP, saponins and saponin derivatives, such as Quil A and QS-21, aluminum hydroxide, and lymphatic cytokine. Preferably, an adjuvant will aid in maintaining the secondary and quaternary structure of the immunogens.

Freund's adjuvant is an emulsion of mineral oil and water which is mixed with the immunogenic substance. Although Freund's adjuvant is powerful, it is usually not administered to humans. Instead, the adjuvant alum (aluminum hydroxide) or ST may be used for administration to a human. The vaccine may be absorbed onto the aluminum hydroxide from which it is slowly released after injection. The vaccine may also be encapsulated within liposomes according to Fullerton, U.S. Pat. No. 4,235,877, or mixed with or liposomes or lipid mixtures to provide an environment similar to the cell surface environment.

In another preferred embodiment, one or more immunogens of the invention are combined with other imnmunogens that are used to vaccinate animals.

In another preferred embodiment, the present invention relates to a method of inducing an immune response in an animal comprising administering to the animal the vaccine of the invention in an amount effective to induce an immune response. Optionally, the vaccine of the invention may be coadministered with effective amounts of other immunogens as mentioned above to generate multiple immune responses in the animal.

Compositions of the invention are useful as vaccines to induce active immunity towards antigens in subjects. Any animal that may experience the beneficial effects of the compositions of the present invention within the scope of subjects that may be treated. The subjects are preferably mammals, and more preferably humans.

The administration of the vaccine may be for either a "prophylactic" or "therapeutic" purpose. When provided prophylactically, the vaccine(s) are provided in advance of any symptoms of HIV infection, or in advance of any known exposure to HIV. The prophylactic administration of the vaccine(s) serves to prevent or attenuate any subsequent infection. When provided therapeutically, the vaccine(s) is provided upon or after the detection of symptoms which indicate that an animal may be infected with HIV, or upon or after exposure to the virus. The therapeutic administration of the vaccine(s) serves to attenuate any actual infection, for example as measured by improving the symptoms of a subject, or by reducing the level of viral replication. Thus, the vaccines, may be provided either prior to the onset of infection (so as to prevent or attenuate an anticipated infection) or after the initiation of an actual infection.

EXAMPLE 1

Immunogens of the Present Invention Elicit a Neutralizing Antibody Response to Entry-Relevant Structures on HIV-1 gp41

Materials and Methods

Polyclonal sera can be obtained by immunizing rabbits or guinea pigs using methods well known to those skilled in the art. For example, the animals are immunized at multiple sites (sub-cutaneous and sub-clavicular) with a total of 200 μg (rabbits) or 100 μg (guinea pigs) of the appropriate peptide, protein, combination of construct in complete Freund's adjuvant. This is followed by two booster immunizations with the same immunogen in incomplete Freund's adjuvant at monthly intervals following the primary immunization. Sera are collected prior to, and at intervals following, the series of immunizations. These sera are analyzed for the presence of antibodies to the immunogen or other antigens by various assays including those described below.

Peptide ELISA: Antigen was coated onto 96-well microtiter plates (Immulon 2) at 1 μg/well. Following overnight incubation at 4° C., plates were washed, blocked and test sera was added. After a 1.5 hr incubation, plates are washed and bound antibody is detected by addition of phosphatase-conjugated secondary antibody and development by pNPP.

Dot Blots: Antigen (2 μg) was blotted onto nitrocellulose, blocked and allowed to air dry. Blots were incubated 4 hr with test sera at a 1:100 dilution. A secondary antibody peroxidase/TMB detection system was used.

Western Blots: Immunoblots were carried out using commercially available strips (Organon Teknika) with test sera at 1:100.

Viral Lysate Immunoprecipitation: HIV-1 infected cells (IIIB/19) were lysed and mixed with immune sera at a dilution of 1:100. Following incubation with Protein A-agarose, immunoprecipitates were separated by SDS-PAGE and probed with a gp41 specific monoclonal antibody.

Cell Surface Immunoprecipitation: Two days post transfection, $1.5\times10^7$ envelope expressing 293T cells were incubated with experimental sera with and without sCD4 (10 μg/ml unless otherwise noted). Following incubation, cells were lysed and incubated with Protein A-agarose. Immunoprecipitates were separated by SDS-PAGE and probed with a gp41 specific monoclonal antibody.

Neutralization Assay: Test sera was incubated at a 1:10 dilution with indicated amount of virus (HIV-1 IIIB) for 1 hr at 37° C. At the end of this time target cells were added (CEM) and the experiment was returned to the incubator. On days 1, 3 and 5, post-infection complete media changes were carried out. On day 7 PI culture supernatant were harvested. Levels of virus replication were determined by p24 antigen capture. Levels of replication in test wells were normalized to virus only controls.

Results

Rabbits or guinea pigs were immunized and sera analyzed by methods described above. The following data describe the characterization of polyclonal antibodies generated to various immunogens that are the subject of this invention.

Table V illustrates results of the analysis of polyclonal sera to various immunogens analyzed by peptide ELISA or dot blots. Several immunogens elicited a strong antibody response in these assays. For example, immunization with P15 resulted in sera with strong antibody reactivity to P15 by peptide ELISA (titer>1:102400), and strong reactivity to P15, a mixture of P15+P16 and HIV-1 gp41 by dot blot. Similar results were obtained in these assays following immunization with a mixture of P15 and P16 (Table V).

Description of Table V: Analysis of polyclonal sera to various immunogens by peptide ELISA or dot blot. For this and subsequent figures all results are based on immunizations of rabbits except for immunizations with P-17 or P-18 alone which were performed in guinea pigs. The immunogens used are indicated in the vertical list on the left side of the table. The antigens used in each assay are indicated on the top row of the table. Peptide ELISA results are presented as titers (the maximum dilution that gives a positive result in the assay). Dot blot results are scored from -(no reactivity) to +++(very strong reactivity). HIV TM is HIV-1 gp41. For Table V, *$BS^3$ refers to chemically cross linked; and ND indicates "not determined."

TABLE VA

| | Dot Blot | | | | | |
|---|---|---|---|---|---|---|
| Immunogen | P15 | P16 | P15 + P16 | P-17 | P-18 | HIV TM |
| P15 | +++ | - | +++ | + | - | +++ |
| P-17 | ND | ND | ND | ND | ND | ND |
| P16 | - | +/- | ++ | - | - | + |
| P-18 | ND | ND | ND | ND | ND | ND |
| P15 + P16 | +++ | + | +++ | +/- | +/- | +++ |
| P-17 + P-18 | - | - | - | ++ | +/- | + |
| P-17 + P-18* | - | - | - | +++ | +/- | ++ |
| P15* | +++ | - | +++ | + | - | ++ |
| P16* | - | + | ++ | +/- | - | ++ |
| HIV TM | ND | ND | ND | ND | ND | ND |

Figure 4:
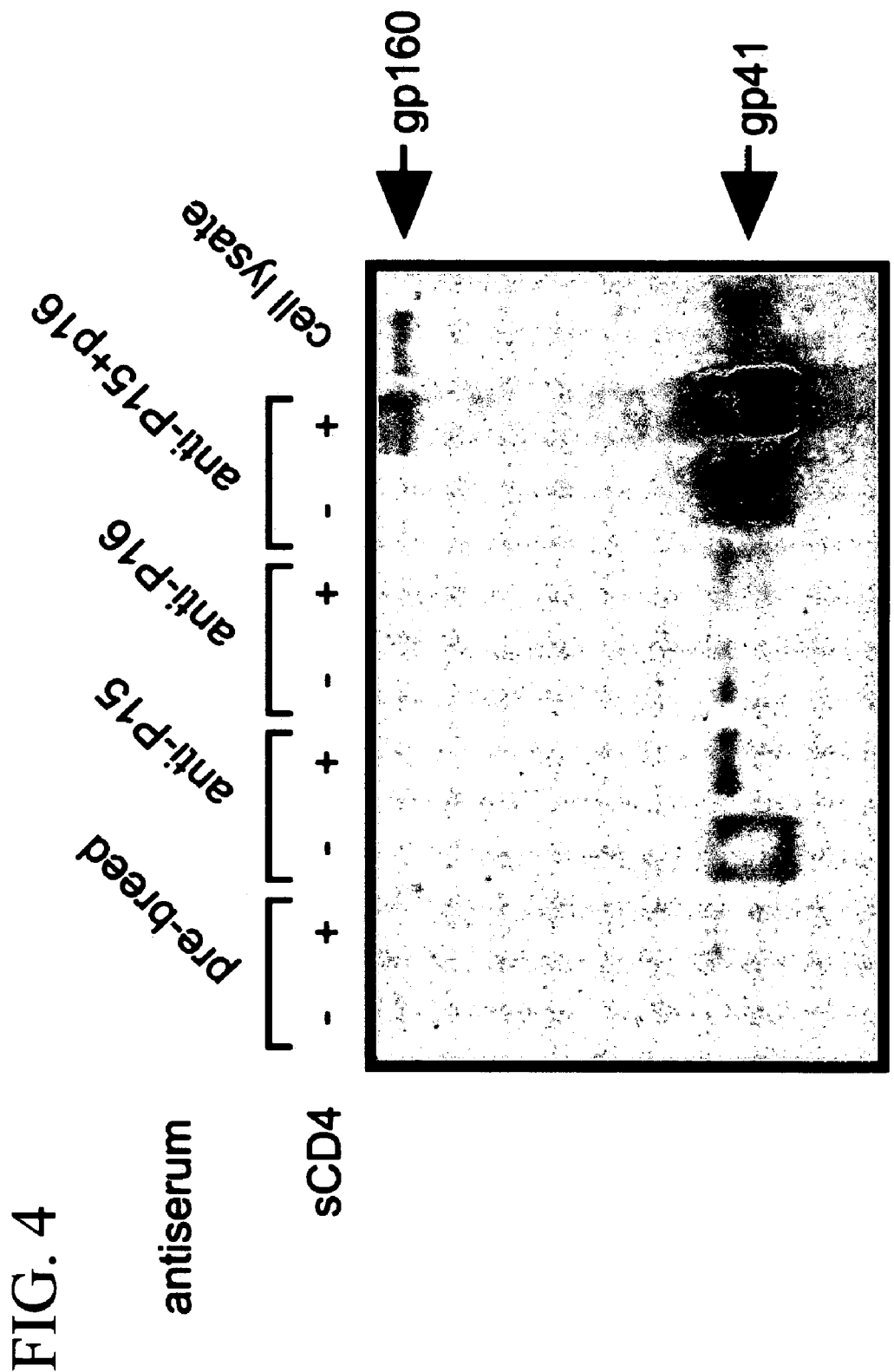
FIG. 4 depicts the analysis of polyclonal sera to various immunogens by surface immunoprecipitation. The precipitations were performed in the presence (+) or absence (−) of 10 µg/ml sCD4.

These results were confirmed and extended by analysis of the polyclonal sera for reactivity with HIV-1 gp120, gp41 or gp160 by western blot or immunoprecipitation (Table VI). For example, immunization with P15 or P15+P16 elicited antibodies that reacted with gp160 by western blot, and which precipitated gp41 in infected cell lysates. Of particular interest, P15+P16 elicited an immune response that reacted with cell surface gp41, but only following treatment of the cells with sCD4 (FIG. 4). Previous reports have found that sCD4 binds to gp120 resulting in conformational changes in gp120/gp41 or stripping of gp120 from gp41. This process presumably mimics events that occur at attachment of HIV-1 to its receptor CD4 on target cells. The present results suggest that immunization with the mixture of P15+P16 elicits an immune response to cryptic epitopes on gp41 that are only exposed following binding of gp120 to CD4. Table VI: Analysis of polyclonal sera to various immunogens by western blot or immunoprecipitation. The immunogens used are indicated in the vertical list on the left side of the table. The antigens used in each assay are indicated on the top row of the table. Results are scored from -(no reactivity) to ++++(very strong reactivity), w: weak reactivity; *: $BS^3$ chemically cross-linked prior to administration; ND: not determined; HIV TM: HIV-1 gp41.

TABLE VI

| | HIV-1 WB | | IP | |
|---|---|---|---|---|
| | gp160 | gp41 | Lysate | Surface |
| P15 | w | w | ++++ | - |
| P-17 | w | w | ++++ | ND |
| P16 | - | - | - | - |
| P-18 | + | w | - | ND |
| P15 + P16 | +++ | ++ | ++++ | + |
| P-17 + P-18 | - | ++ | - | ND |
| P-17 + P-18* | w | - | - | ND |
| P15* | w | - | +++ | - |
| P16* | + | - | - | ND |
| HIV TM | +++ | ++ | ++++ | ND |

Figure 5B:
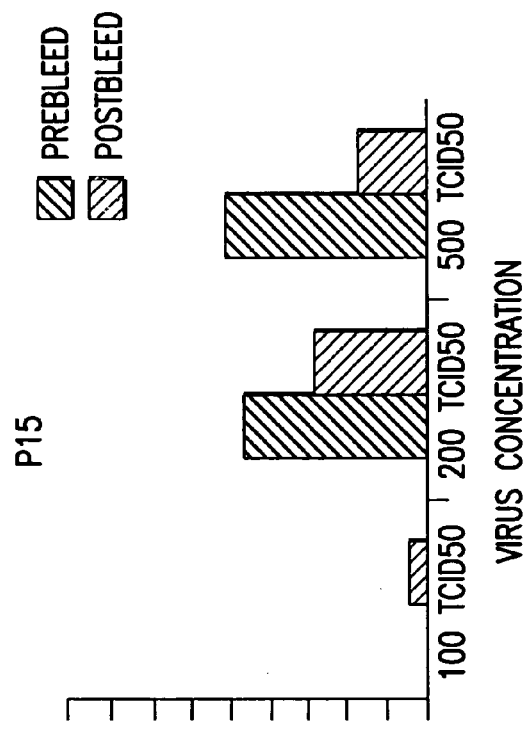
FIG. 5 depicts analysis of polyclonal sera to various immunogens in neutralization assays. Immune seraorpreimmune (prebleed) sera were diluted 1:10 and incubated with various concentrations of virus (indicated in numbers of tissue culture infectious doses—TCID50). Levels of virus replication were measured by the amount of p24 in the supernatant seven days following infection, and normalized to the degree of replication in the absence of any rabbit serum. The positive (+ve) control used is a strongly neutralizing serum from an HIV-1 infected individual.
Figure 5A:
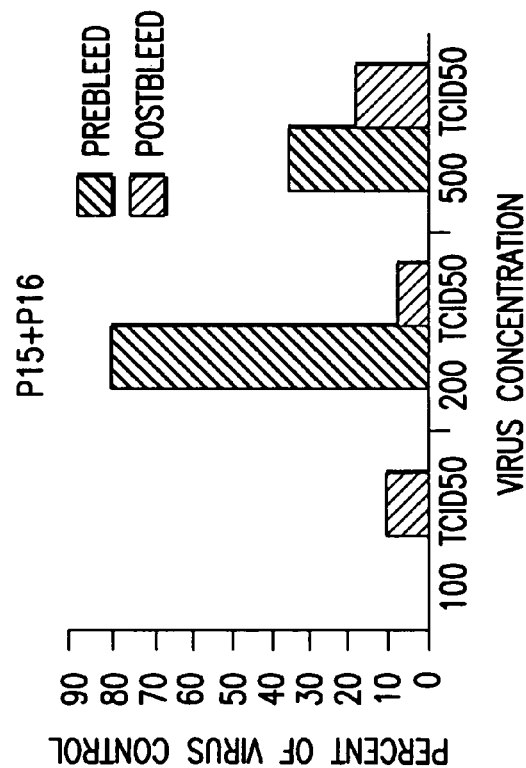

FIG. 5 provides data demonstrating that immunogens of the present invention elicit a neutralizing antibody response. While some non-specific inhibition of HIV-1 replication is seen following incubation with pre-bleed sera, considerably greater inhibition is seen following incubation with sera from animals immunized with P15 or P 15+P 16. These results indicate that these sera contain neutralizing antibodies resulting from immunization with the immunogen of, and by the methods of, the current invention.

TABLE Vb

| | Peptide ELISA | | | | | | | |
|---|---|---|---|---|---|---|---|---|
| Immunogen | P15 | P16 | P15 + P16 | P-17 | P-18 | P-17/P-18 | P-15/P-18 | gp41 |
| P15 | 1:1.6 × $10^6$ | 1:1600 | 1:1.6 × $10^6$ | ~1:800 | ND | ND | ND | 1:6400 |
| P-17 | ND | ND | ND | 1:4.1 × $10^5$ | ND | 1:4.1 × $10^5$ | ND | 1:25600 |
| P16 | >1:1600 | 1:1.0 × $10^5$ | 1:25600 | ND | ~1:800 | ND | ND | 1:1600 |
| P-18 | ND | ND | ND | ND | 1:25600 | 1:1.0 × $10^5$ | ND | 1:25,600 |
| P15 + P16 | 1:4.1 × $10^5$ | 1:4.1 × $10^5$ | 1:4.1 × $10^5$ | <1:100 | >1:3200 | ND | ND | 1:4.1 × $10^5$ |
| P-17 + P-18 | ND | ND | >1:200 | 1:25600 | 1:6400 | 1:1.0 × $10^5$ | ND | 1:1600 |
| P-17 + P-18* | ND | ND | >1:100 | 1:1600 | <1:1600 | ND | ND | ND |
| P15* | 1:12800 | ND | >1:25600 | ND | ND | ND | ND | ND |
| P16* | ND | 1:25600 | >1:25600 | ND | ND | ND | ND | ND |
| P-15/P-18 | 1:4.1 × $10^5$ | ND | ND | ND | 1:6400 | ND | 1:4.1 × $10^5$ | 1:25600 |
| HIV TM | 1:25600 | >1:6400 | ND | 1:400 | 1:1600 | | | |

These data are supported by the fact that monoclonal antibodies have been generated in mice to several of the immunogens discussed above. When analyzed by some of the methods described above similar results were obtained to those seen with the polyclonal sera (not shown).

Discussion

The structural components of gp41, which are present only during virus entry, form a novel set of neutralizing epitopes. The relatively short lived nature of these entry relevant structures and their presence only during natural infection would account for the observation that neutralizing antibodies targeting gp41 epitopes are poorly represented in sera from HIV infected individuals and all but absent in vaccine sera. This theory is supported by work involving synthetic peptides which model the regions of gp41 identified as taking part in the entry related structural reorganization (Wild, C., et al., *Proc. Natl. Acad. Sci. USA* 89:10537-10541 (1992); Wild, C., et al., *AIDS Res. Hum. Retroviruses* 9:1051-1053 (1993); Wild, C., et al., *Proc. Natl. Acad. Sci. USA* 91:12676-12680 (1994); Wild, C., et al., *AIDS Res. Hum. Retroviruses* 11:323-325 (1995); Wild, C., et al., *Proc. Natl. Acad. Sci. USA* 91:9770-9774 (1994)). It has been shown that these materials inhibit HIV infection by blocking virus entry and the mechanism of their activity is their ability to interact with and disrupt gp41 structural components critical to the entry event. Although transitory, these gp41 entry structures are both accessible and appropriately sensitive targets for neutralizing antibody.

Independent of their neutralizing potential, monoclonal antibodies targeted to conserved structures in the TM will prove invaluable as reagents for dissecting the structural transitions that occur in Env as part of virus entry.

We have been successful in our initial attempt to generate a structure specific antibody against the coiled-coil region of gp41. In this work we used a modified form of the P-17 peptide as immunogen and generated MAbs that recognize the structured peptide but not a proline containing P-17 analog which is unstructured. Also, this antibody can co-immunoprecipitate the P-18 peptide.

EXAMPLE 2

Neutralizing Antibody Response to Peptides Modeling the C-helical Region of gp41

This example measures the humoral response to antigens modeling the C-region of gp41. This work used synthetic peptides and a recombinant form of viral protein to characterize antibodies raised against the C-helical regions of gp41 of the viral TM.

These studies employ antibody binding assays to determine the ability of these materials to generate an immune response to various forms of envelope (native vs. denatured) and virus neutralization assays to characterize the antibody response raised against these gp41 domains. The complete panel of immunogens has generated data which allow new insight into the antigenic nature of gp41. Most encouraging have been the results from Guinea Pigs immunized with the peptide, P-1 8, modeling the C-helix entry domain (amino acid residues 643-678 of gp41). Specifically, two of three animals receiving this material exhibited a neutralizing antibody response against divergent virus isolates in a variety of assay formats. Additional studies have confirmed these results. See Example 3.

In study 1, guinea pigs were immunized intramuscularly with 100 μg of P-18 formulated in either Freund's complete (prime) or incomplete (boost) adjuvant. Animals were immunized on days 0, 21, 34, 48 and 62. Blood was collected on days 44, 58 and 72. In the initial screen, sera at at 1:10 dilution were tested for ability to inhibit virus-induced cell killing. In these assays two of the three animals receiving the P-18 peptide (guinea pigs gp233 and gp234) were able to block the cytopathic effects of a pair of prototype HIV-1 isolates. Against the MN isolate >80% protection was achieved while against RF protection was >50%.

Figure 6B:
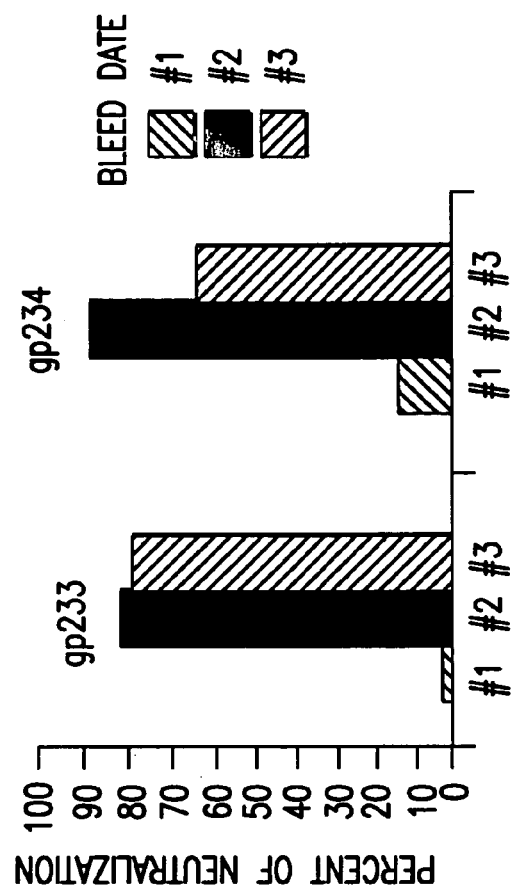
FIG. 6b shows the percent neutralization for each bleed at a 1:10 dilution against HIV-$1_{MN}$ in an assay format employing CEM targets and p24 endpoint. In this assay, sera are incubated with 200 TCID$_{50}$ of virus for 1 hr prior to the addition of cells. On days 1, 3, and 5 media are changed. On day 7 culture supernatants are collected and analyzed for virus replication by p24 antigen levels. In each assay format, percent neutralization is determined by comparison of experimental wells with cell and cell/virus controls.
Figure 6A:
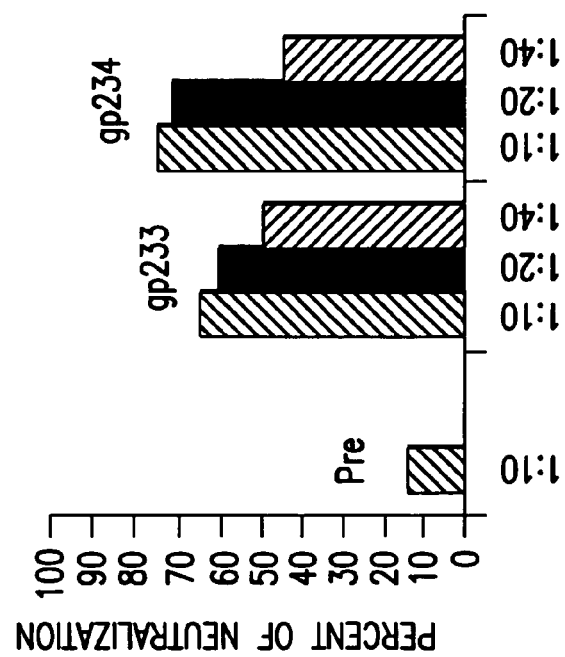
FIG. 6a shows the titration of bleed 2 for each animal against HIV-$1_{MN}$ in the cell killing assay which uses cell viability as a measure of virus neutralization. MT2 cells are added to a mixture of virus (sufficient to result in greater than 80% cell death at 5 days post infection) and sera which had been allowed to incubate for approximately 1 hr. After 5 days in culture, cell viability is measured by vital dye metabolism.

In an assay employing the same format (against HIV-$1_{MN}$), we titrated the sera from gp233 and gp234. As can be seen in FIG. 6a, these animals displayed the expected dose-related anti-viral activity. Guinea pigs 233 and 234 gave a 50% reduction in virus-induced cell killing at 1:40 and 1:37 dilutions, respectively.

A neutralization assay was carried out employing a different target cell and endpoint analysis. In this format, CEM T-cell line was inoculated with 200 $TCID_{50}$ of the HIV-$1_{MN}$ isolate. The reduction in viral replication for gp233 and gp234 at a serum dilution of 1:10 is shown in FIG. 6b.

FIG. 6a shows the titration of bleed 2 for each animal against HIV-$1_{MN}$ in the cell killing assay which uses cell viability as a measure of virus neutralization. MT2 cells are added to a mixture of virus (sufficient to result in greater than 80% cell death at 5 days post infection) and sera which had been allowed to incubate for approximately 1 hr. After 5 days in culture, cell viability is measured by vital dye metabolism. FIG. 6b shows the percent neutralization for each bleed at a 1:10 dilution against HIV-$1_{MN}$ in an assay format employing CEM targets and p24 endpoint. In this assay, sera are incubated with 200 $TCID_{50}$ of virus for 1 hr prior to the addition of cells. On days 1, 3, and 5 media are changed. On day 7 culture supernatants are collected and analyzed for virus replication by p24 antigen levels. In each assay format, percent neutralization is determined by comparison of experimental wells with cell and cell/virus controls.

The pattern of virus neutralization observed in the previous assays is repeated. At this serum dilution, bleed #2 for guinea pigs 233 and 234 gave 80% and 90% virus neutralization, respectively. The same pattern of results was observed against the HIV-$1_{SF2}$ isolate where under identical assay conditions bleed #2 from animals 233 and 234 gave 70% and 50% neutralization. Control animals receiving adjuvant only exhibited no neutralizing activity.

These sera neutralize the HIV-1 isolates MN, RF, and SF2. These results indicate a breadth of activity unseen in most other subunit immunogens. By comparison, sera generated against V3 peptides are restricted in their activity to a small set of very closely related isolates. Due to the nature of the experiment the low antibody titers are not unexpected. These animals were immunized with free peptide formulated in Freund's adjuvant. Neither carrier molecules nor accessory proteins were used to enhance the immune response to this molecule. Results from binding assays indicate low but appreciable levels of antibody against viral envelope.

In ELISA assays using recombinant gp41 endpoint titers of 1:6400-1:44,800 were observed for these samples. Linking P-18 to KLH (or other carrier molecules) and/or administering the conjugate in an adjuvant designed to enhance the immunogenicity of subunit antigens is expected to result in a significant increase in neutralizing response.

EXAMPLE 3

In a second study, 2 out of 3 animals immunized with P-18 neutralized the HIV-1 MN isolate in the assay using the MT2 cell line.

| animal | neut50 titer |
|---|---|
| BT 004 | 1:21 |
| BT 005 | 1:14 |

Also, one animal receiving P-18 coupled to KLH neutralized the MN isolate in the same assay format.

| animal | neut50 titer |
|---|---|
| BT 007 | 1:15 |

EXAMPLE 4

The peptide used to generate the immune response in Example 2 includes within its sequence the linear epitope for the 2F5 monoclonal antibody. To determine if our immune response was against this same region of envelope, or involved a previously unidentified neutralizing epitope, a series of binding experiments was carried out to characterize the reactivity of our polyclonal sera. As can be seen in Table 1, at a dilution of 1:100 all animals exhibit good ELISA binding to the cognate immunogen (P-18). Sera from these animals also have substantial antibody titers against a peptide derived from the N-terminal P-18 sequence, P1 (Table VII). However, when tested at this same dilution against a pair of C-terminal P-18 analogs, P2 and P3 (Table VII) no ELISA reactivity was observed (Table VI). This result is significant in that the P3 peptide includes the linear binding region (ELDKWAS) for the 2F5 monoclonal antibody. These results demonstrate that the neutralizing activity in our sera is not due to binding to the 2F5 epitope.

TABLE VII

Set of three overlapping peptides corresponding to the P-18 peptide

| | | |
|---|---|---|
| P1 | YTSLIHSLIEESQNQQEK | (SEQ ID NO:77) |
| P2 | EESQNQQEKNEQELLELD | (SEQ ID NO:78) |
| P3 | LELDKWASLWNWF | (SEQ ID NO:79) |
| P-18 | YTSLIHSLIEESQNQQEKNEQELLELDKWASLWNWF | (SEQ ID NO:5) |

TABLE VIII

ELISA binding at 1:100 (OD)

| Sample | P1 | P2 | P3 | P-18 |
|---|---|---|---|---|
| gp232-2 | 0.833 | 0.124 | 0.003 | 1.423 |
| gp232-3 | 0.858 | 0.022 | 0.009 | 1.067 |
| gp233-2 | 1.024 | 0.019 | 0.010 | 1.314 |
| gp233-3 | 0.885 | 0.015 | 0.015 | 1.161 |
| gp234-2 | 0.492 | 0.015 | 0.016 | 1.152 |
| gp234-3 | 0.796 | 0.012 | 0.009 | 0.913 |

ELISA binding by guinea pig sera to P-18 and a set of overlapping peptides corresponding to P-18. The majority of the antibody binding is to P-18 and the N-terminal peptide P1. Very little or no reactivity is observed against P2 and P3 modeling the C-terminal region of P-18.

EXAMPLE 5

Expression of Recombinant gp41 Construct

The plasmid for expression of the construct containing the N- and C-helical domains of HIV-1 gp41 separated by a short linker sequence (See FIG. 7) was prepared as follows. The bacterial expression vector pTCLE-ssG2C, (based on pAED4, a T7 expression vector developed specifically for the expression of small proteins) provided by Dr. Terrance Oas, Duke University was digested at the unique restriction sites NdeI and EcorI and gel purified using the Qiaex system. The DNA fragments encoding the N- and C-helical regions of HIV-1 gp41 and a short linker sequence were PCR amplified by standard techniques from gp41 expression vectors using the following primers. N-helix primer pair:

```
5'; 5' GGG CCC ATA TGG GTA TTG TTC    (SEQ ID NO:80)

AGC AG 3' (includes NdeI site),

3'; 5' GGG CCG GCG CCT GAG CCG CCG    (SEQ ID NO:81)

CCT TGA TCC TTC AGG TAG CGT TC 3'

(includes NarI site).

C-helix primer pair:
5'; 5' GGG CCG GCG CCG GCT CAG AGT    (SEQ ID NO:82)

GGG ACA GAG AAA TTA ACA ATT AC 3'

(includes NarI site),
```

-continued
```
3'; 5' GGG CCG AAT TCT TAA AAC CAA    (SEQ ID NO:83)

TTC CAC AAA CTT GCC CAT TT 3'

(includes EcorI site and a stop codon).
```

These fragments were inserted (blunt end ligation) into the TA vector which was amplified to generate larger amounts of DNA. The fragments coding for to the N and C-helices were released from the TA vector by restriction digest (C-helix: NarI and EcoRI, N-helix: NdeI and NarI) and gel purified. A three-way ligation was performed using standard procedures to introduce the DNA coding for the N- and C-helical fragments into the pTCLE-ssG2C vector. The product of this step was characterized by restriction digestion and DNA sequencing. The vector containing the desired gp41 coding region was prepared in large quantity and BL-21 *E. coli* host cells were transformed and induced to express the desired protein. The desired proteins may or may not have a methionine as the first amino acid at he N-terminus. Over-expression of a protein of the appropriate molecular weight was observed by SDS-Page gel electrophoresis.

Although the foregoing refers to particular preferred embodiments, it will be understood that the present -continued Ala Arg Ile Leu
            35

<210> SEQ ID NO 4
<211> LENGTH: 56
<212> TYPE: PRT
<213> ORGANISM: Human immunodeficiency virus

<400> SEQUENCE: 4

Trp Asn Asn Met Thr Trp Met Glu Trp Asp Arg Glu Ile Asn Asn Tyr
  1               5                  10                  15

Thr Ser Leu Ile His Ser Leu Ile Glu Glu Ser Gln Asn Gln Gln Glu
             20                  25                  30

Lys Asn Glu Gln Glu Leu Leu Glu Leu Asp Lys Trp Ala Ser Leu Trp
         35                  40                  45

Asn Trp Phe Asn Ile Thr Asn Trp
     50                  55

<210> SEQ ID NO 5
<211> LENGTH: 36
<212> TYPE: PRT
<213> ORGANISM: Human immunodeficiency virus type 1

<400> SEQUENCE: 5

Tyr Thr Ser Leu Ile His Ser Leu Ile Glu Glu Ser Gln Asn Gln Gln
  1               5                  10                  15

Glu Lys Asn Glu Gln Glu Leu Leu Glu Leu Asp Lys Trp Ala Ser Leu
             20                  25                  30

Trp Asn Trp Phe
         35

<210> SEQ ID NO 6
<211> LENGTH: 34
<212> TYPE: PRT
<213> ORGANISM: Artificial Sequence
<220> FEATURE:
<223> OTHER INFORMATION: Description of Artificial Sequence:Synthetic

<400> SEQUENCE: 6

Trp Met Glu Trp Asp Arg Glu Ile Asn Asn Tyr Thr Ser Leu Ile His
  1               5                  10                  15

Ser Leu Ile Glu Glu Ser Gln Asn Gln Gln Glu Lys Asn Glu Gln Glu
             20                  25                  30

Leu Leu

<210> SEQ ID NO 7
<211> LENGTH: 5
<212> TYPE: DNA
<213> ORGANISM: Artificial Sequence
<220> FEATURE:
<223> OTHER INFORMATION: Description of Artificial Sequence:Synthetic

<400> SEQUENCE: 7 ggggs                                                             5

<210> SEQ ID NO 8
<211> LENGTH: 345
<212> TYPE: PRT
<213> ORGANISM: Human immunodeficiency virus type 1

<400> SEQUENCE: 8

Ala Val Gly Ile Gly Ala Leu Phe Leu Gly Phe Leu Gly Ala Ala Gly

```
                1               5              10              15
Ser Thr Met Gly Ala Arg Ser Met Thr Leu Thr Val Gln Ala Arg Gln
                   20                  25                  30

Leu Leu Ser Gly Ile Val Gln Gln Asn Asn Leu Leu Arg Ala Ile
                   35                  40                  45

Glu Ala Gln Gln His Leu Leu Gln Leu Thr Val Trp Gly Ile Lys Gln
             50                  55                  60

Leu Gln Ala Arg Ile Leu Ala Val Glu Arg Tyr Leu Lys Asp Gln Gln
 65                      70                  75                  80

Leu Leu Gly Ile Trp Gly Cys Ser Gly Lys Leu Ile Cys Thr Thr Ala
                    85                  90                  95

Val Pro Trp Asn Ala Ser Trp Ser Asn Lys Ser Leu Glu Gln Ile Trp
                  100                 105                 110

Asn Asn Met Thr Trp Met Glu Trp Asp Arg Glu Ile Asn Asn Tyr Thr
                  115                 120                 125

Ser Leu Ile His Ser Leu Ile Glu Glu Ser Gln Asn Gln Gln Glu Lys
                  130                 135                 140

Asn Glu Gln Glu Leu Leu Glu Leu Asp Lys Trp Ala Ser Leu Trp Asn
145                 150                 155                 160

Trp Phe Asn Ile Thr Asn Trp Leu Trp Tyr Ile Lys Ile Phe Ile Met
                  165                 170                 175

Ile Val Gly Gly Leu Val Gly Leu Arg Ile Val Phe Ala Val Leu Ser
                  180                 185                 190

Ile Val Asn Arg Val Arg Gln Gly Tyr Ser Pro Leu Ser Phe Gln Thr
                  195                 200                 205

His Leu Pro Thr Pro Arg Gly Pro Asp Arg Pro Glu Gly Ile Glu Glu
                  210                 215                 220

Glu Gly Gly Glu Arg Asp Arg Asp Arg Ser Ile Arg Leu Val Asn Gly
225                 230                 235                 240

Ser Leu Ala Leu Ile Trp Asp Asp Leu Arg Ser Leu Cys Leu Phe Ser
                  245                 250                 255

Tyr His Arg Leu Arg Asp Leu Leu Leu Ile Val Thr Arg Ile Val Glu
                  260                 265                 270

Leu Leu Gly Arg Arg Gly Trp Glu Ala Leu Lys Tyr Trp Trp Asn Leu
                  275                 280                 285

Leu Gln Tyr Trp Ser Gln Glu Leu Lys Asn Ser Ala Val Ser Leu Leu
                  290                 295                 300

Asn Ala Thr Ala Ile Ala Val Ala Glu Gly Thr Asp Arg Val Ile Glu
305                 310                 315                 320

Val Val Gln Gly Ala Cys Arg Ala Ile Arg His Ile Pro Arg Arg Ile
                  325                 330                 335

Arg Gln Gly Leu Glu Arg Ile Leu Leu
                  340                 345

<210> SEQ ID NO 9
<211> LENGTH: 45
<212> TYPE: PRT
<213> ORGANISM: Artificial Sequence
<220> FEATURE:
<223> OTHER INFORMATION: Description of Artificial Sequence:Synthetic

<400> SEQUENCE: 9

Ser Gly Ile Val Gln Gln Asn Asn Leu Leu Arg Ala Ile Glu Ala
  1               5                  10                  15

Gln Gln His Leu Leu Gln Leu Thr Val Trp Gly Ile Lys Gln Leu Gln
```

```
                    20                  25                  30

Ala Arg Ile Leu Ala Val Glu Arg Tyr Leu Lys Asp Gln
        35                  40                  45

<210> SEQ ID NO 10
<211> LENGTH: 45
<212> TYPE: PRT
<213> ORGANISM: Artificial Sequence
<220> FEATURE:
<223> OTHER INFORMATION: Description of Artificial Sequence:Synthetic

<400> SEQUENCE: 10

Ser Gly Ile Val Gln Gln Gln Asn Asn Leu Leu Arg Ala Ile Glu Ala
 1               5                  10                  15

Gln Gln His Leu Leu Gln Leu Thr Val Trp Gly Ile Lys Gln Leu Gln
            20                  25                  30

Ala Arg Val Leu Ala Leu Glu Arg Tyr Leu Arg Asp Gln
        35                  40                  45

<210> SEQ ID NO 11
<211> LENGTH: 36
<212> TYPE: PRT
<213> ORGANISM: Artificial Sequence
<220> FEATURE:
<223> OTHER INFORMATION: Description of Artificial Sequence:Synthetic

<400> SEQUENCE: 11

Ser Gly Ile Val Gln Gln Gln Asn Asn Leu Leu Arg Ala Ile Glu Ala
 1               5                  10                  15

Gln Gln His Leu Leu Gln Leu Thr Val Trp Gly Ile Lys Gln Leu Gln
            20                  25                  30

Ala Arg Val Leu
        35

<210> SEQ ID NO 12
<211> LENGTH: 38
<212> TYPE: PRT
<213> ORGANISM: Artificial Sequence
<220> FEATURE:
<223> OTHER INFORMATION: Description of Artificial Sequence:Synthetic

<400> SEQUENCE: 12

Asn Asn Leu Leu Arg Ala Ile Glu Ala Gln Gln His Leu Leu Gln Leu
 1               5                  10                  15

Thr Val Trp Gly Ile Lys Gln Leu Gln Ala Arg Val Leu Ala Leu Glu
            20                  25                  30

Arg Tyr Leu Arg Asp Gln
        35

<210> SEQ ID NO 13
<211> LENGTH: 45
<212> TYPE: PRT
<213> ORGANISM: Artificial Sequence
<220> FEATURE:
<223> OTHER INFORMATION: Description of Artificial Sequence:Synthetic

<400> SEQUENCE: 13

Ser Gly Ile Val Gln Gln Gln Asn Asn Leu Leu Arg Ala Ile Glu Ala
 1               5                  10                  15

Gln Gln Arg Met Leu Gln Leu Thr Val Trp Gly Ile Lys Gln Leu Gln
            20                  25                  30

Ala Arg Val Leu Ala Val Glu Arg Tyr Leu Gly Asp Gln
```

```
              35                  40                  45

<210> SEQ ID NO 14
<211> LENGTH: 36
<212> TYPE: PRT
<213> ORGANISM: Artificial Sequence
<220> FEATURE:
<223> OTHER INFORMATION: Description of Artificial Sequence:Synthetic

<400> SEQUENCE: 14

Ser Gly Ile Val Gln Gln Gln Asn Asn Leu Leu Arg Ala Ile Glu Ala
 1               5                  10                  15

Gln Gln Arg Met Leu Gln Leu Thr Val Trp Gly Ile Lys Gln Leu Gln
            20                  25                  30

Ala Arg Val Leu
        35

<210> SEQ ID NO 15
<211> LENGTH: 38
<212> TYPE: PRT
<213> ORGANISM: Artificial Sequence
<220> FEATURE:
<223> OTHER INFORMATION: Description of Artificial Sequence:Synthetic

<400> SEQUENCE: 15

Asn Asn Leu Leu Arg Ala Ile Glu Ala Gln Gln Arg Met Leu Gln Leu
 1               5                  10                  15

Thr Val Trp Gly Ile Lys Gln Leu Gln Ala Arg Val Leu Ala Val Glu
            20                  25                  30

Arg Tyr Leu Gly Asp Gln
        35

<210> SEQ ID NO 16
<211> LENGTH: 45
<212> TYPE: PRT
<213> ORGANISM: Artificial Sequence
<220> FEATURE:
<223> OTHER INFORMATION: Description of Artificial Sequence:Synthetic

<400> SEQUENCE: 16

Ser Gly Ile Val Gln Gln Gln Asn Asn Leu Leu Arg Ala Ile Glu Ala
 1               5                  10                  15

Gln Gln His Met Leu Gln Leu Thr Val Trp Gly Ile Lys Gln Leu Gln
            20                  25                  30

Ala Arg Val Leu Ala Leu Glu Arg Tyr Leu Arg Asp Gln
        35                  40                  45

<210> SEQ ID NO 17
<211> LENGTH: 36
<212> TYPE: PRT
<213> ORGANISM: Artificial Sequence
<220> FEATURE:
<223> OTHER INFORMATION: Description of Artificial Sequence:Synthetic

<400> SEQUENCE: 17

Ser Gly Ile Val Gln Gln Gln Asn Asn Leu Leu Arg Ala Ile Glu Ala
 1               5                  10                  15

Gln Gln His Met Leu Gln Leu Thr Val Trp Gly Ile Lys Gln Leu Gln
            20                  25                  30

Ala Arg Val Leu
        35
```

<210> SEQ ID NO 18
<211> LENGTH: 38
<212> TYPE: PRT
<213> ORGANISM: Artificial Sequence
<220> FEATURE:
<223> OTHER INFORMATION: Description of Artificial Sequence:Synthetic

<400> SEQUENCE: 18

Asn Asn Leu Leu Arg Ala Ile Glu Ala Gln Gln His Met Leu Gln Leu
 1               5                  10                  15

Thr Val Trp Gly Ile Lys Gln Leu Gln Ala Arg Val Leu Ala Leu Glu
            20                  25                  30

Arg Tyr Leu Arg Asp Gln
        35

<210> SEQ ID NO 19
<211> LENGTH: 45
<212> TYPE: PRT
<213> ORGANISM: Artificial Sequence
<220> FEATURE:
<223> OTHER INFORMATION: Description of Artificial Sequence:Synthetic

<400> SEQUENCE: 19

Ser Gly Ile Val Gln Gln Gln Ser Asn Leu Leu Arg Ala Ile Glu Ala
 1               5                  10                  15

Gln Gln His Met Leu Gln Leu Thr Val Trp Gly Ile Lys Gln Leu Gln
            20                  25                  30

Ala Arg Val Leu Ala Ile Glu Arg Tyr Leu Arg Asp Gln
        35                  40                  45

<210> SEQ ID NO 20
<211> LENGTH: 36
<212> TYPE: PRT
<213> ORGANISM: Artificial Sequence
<220> FEATURE:
<223> OTHER INFORMATION: Description of Artificial Sequence:Synthetic

<400> SEQUENCE: 20

Ser Gly Ile Val Gln Gln Gln Ser Asn Leu Leu Arg Ala Ile Glu Ala
 1               5                  10                  15

Gln Gln His Met Leu Gln Leu Thr Val Trp Gly Ile Lys Gln Leu Gln
            20                  25                  30

Ala Arg Val Leu
        35

<210> SEQ ID NO 21
<211> LENGTH: 38
<212> TYPE: PRT
<213> ORGANISM: Artificial Sequence
<220> FEATURE:
<223> OTHER INFORMATION: Description of Artificial Sequence:Synthetic

<400> SEQUENCE: 21

Ser Asn Leu Leu Arg Ala Ile Glu Ala Gln Gln His Met Leu Gln Leu
 1               5                  10                  15

Thr Val Trp Gly Ile Lys Gln Leu Gln Ala Arg Val Leu Ala Ile Glu
            20                  25                  30

Arg Tyr Leu Arg Asp Gln
        35

<210> SEQ ID NO 22
<211> LENGTH: 45
<212> TYPE: PRT

-continued

<213> ORGANISM: Artificial Sequence
<220> FEATURE:
<223> OTHER INFORMATION: Description of Artificial Sequence:Synthetic

<400> SEQUENCE: 22

Ser Gly Ile Val Gln Gln Gln Asn Asn Leu Leu Arg Ala Ile Glu Ala
 1               5                  10                  15

Gln Gln His Leu Leu Gln Leu Thr Val Trp Gly Ile Lys Gln Leu Gln
            20                  25                  30

Ala Arg Val Leu Ala Val Glu Ser Tyr Leu Lys Asp Gln
        35                  40                  45

<210> SEQ ID NO 23
<211> LENGTH: 38
<212> TYPE: PRT
<213> ORGANISM: Artificial Sequence
<220> FEATURE:
<223> OTHER INFORMATION: Description of Artificial Sequence:Synthetic

<400> SEQUENCE: 23

Asn Asn Leu Leu Arg Ala Ile Glu Ala Gln Gln His Leu Leu Gln Leu
 1               5                  10                  15

Thr Val Trp Gly Ile Lys Gln Leu Gln Ala Arg Val Leu Ala Val Glu
            20                  25                  30

Ser Tyr Leu Lys Asp Gln
        35

<210> SEQ ID NO 24
<211> LENGTH: 45
<212> TYPE: PRT
<213> ORGANISM: Artificial Sequence
<220> FEATURE:
<223> OTHER INFORMATION: Description of Artificial Sequence:Synthetic

<400> SEQUENCE: 24

Ser Gly Ile Val Gln Gln Gln Ser Asn Leu Leu Arg Ala Ile Glu Ala
 1               5                  10                  15

Gln Gln His Leu Leu Gln Leu Thr Val Trp Gly Ile Lys Gln Leu Gln
            20                  25                  30

Ala Arg Val Leu Ala Val Glu Arg Tyr Leu Gln Asp Gln
        35                  40                  45

<210> SEQ ID NO 25
<211> LENGTH: 36
<212> TYPE: PRT
<213> ORGANISM: Artificial Sequence
<220> FEATURE:
<223> OTHER INFORMATION: Description of Artificial Sequence:Synthetic

<400> SEQUENCE: 25

Ser Gly Ile Val Gln Gln Gln Ser Asn Leu Leu Arg Ala Ile Glu Ala
 1               5                  10                  15

Gln Gln His Leu Leu Gln Leu Thr Val Trp Gly Ile Lys Gln Leu Gln
            20                  25                  30

Ala Arg Val Leu
        35

<210> SEQ ID NO 26
<211> LENGTH: 38
<212> TYPE: PRT
<213> ORGANISM: Artificial Sequence
<220> FEATURE:
<223> OTHER INFORMATION: Description of Artificial Sequence:Synthetic

<400> SEQUENCE: 26

Ser Asn Leu Leu Arg Ala Ile Glu Ala Gln Gln His Leu Leu Gln Leu
1               5                   10                  15

Thr Val Trp Gly Ile Lys Gln Leu Gln Ala Arg Val Leu Ala Val Glu
            20                  25                  30

Arg Tyr Leu Gln Asp Gln
        35

<210> SEQ ID NO 27
<211> LENGTH: 45
<212> TYPE: PRT
<213> ORGANISM: Artificial Sequence
<220> FEATURE:
<223> OTHER INFORMATION: Description of Artificial Sequence:Synthetic

<400> SEQUENCE: 27

Ser Gly Ile Val Gln Gln Gln Ser Asn Leu Leu Arg Ala Ile Glu Ala
1               5                   10                  15

Gln Gln His Leu Leu Gln Leu Thr Val Trp Gly Ile Lys Gln Leu Gln
            20                  25                  30

Ala Arg Val Leu Ala Leu Glu Arg Tyr Leu Arg Asp Gln
        35                  40                  45

<210> SEQ ID NO 28
<211> LENGTH: 38
<212> TYPE: PRT
<213> ORGANISM: Artificial Sequence
<220> FEATURE:
<223> OTHER INFORMATION: Description of Artificial Sequence:Synthetic

<400> SEQUENCE: 28

Ser Asn Leu Leu Arg Ala Ile Glu Ala Gln Gln His Leu Leu Gln Leu
1               5                   10                  15

Thr Val Trp Gly Ile Lys Gln Leu Gln Ala Arg Val Leu Ala Leu Glu
            20                  25                  30

Arg Tyr Leu Arg Asp Gln
        35

<210> SEQ ID NO 29
<211> LENGTH: 45
<212> TYPE: PRT
<213> ORGANISM: Artificial Sequence
<220> FEATURE:
<223> OTHER INFORMATION: Description of Artificial Sequence:Synthetic

<400> SEQUENCE: 29

Ser Gly Ile Val Gln Gln Gln Ser Asn Leu Leu Arg Ala Ile Gln Ala
1               5                   10                  15

Gln Gln His Met Leu Gln Leu Thr Val Trp Gly Val Lys Gln Leu Gln
            20                  25                  30

Ala Arg Val Leu Ala Val Glu Arg Tyr Leu Lys Asp Gln
        35                  40                  45

<210> SEQ ID NO 30
<211> LENGTH: 36
<212> TYPE: PRT
<213> ORGANISM: Artificial Sequence
<220> FEATURE:
<223> OTHER INFORMATION: Description of Artificial Sequence:Synthetic

<400> SEQUENCE: 30

-continued

Ser Gly Ile Val Gln Gln Gln Ser Asn Leu Leu Arg Ala Ile Gln Ala
1               5                   10                  15

Gln Gln His Met Leu Gln Leu Thr Val Trp Gly Val Lys Gln Leu Gln
            20                  25                  30

Ala Arg Val Leu
        35

<210> SEQ ID NO 31
<211> LENGTH: 38
<212> TYPE: PRT
<213> ORGANISM: Artificial Sequence
<220> FEATURE:
<223> OTHER INFORMATION: Description of Artificial Sequence:Synthetic

<400> SEQUENCE: 31

Ser Asn Leu Leu Arg Ala Ile Gln Ala Gln Gln His Met Leu Gln Leu
1               5                   10                  15

Thr Val Trp Gly Val Lys Gln Leu Gln Ala Arg Val Leu Ala Val Glu
            20                  25                  30

Arg Tyr Leu Lys Asp Gln
        35

<210> SEQ ID NO 32
<211> LENGTH: 45
<212> TYPE: PRT
<213> ORGANISM: Artificial Sequence
<220> FEATURE:
<223> OTHER INFORMATION: Description of Artificial Sequence:Synthetic

<400> SEQUENCE: 32

Ser Gly Ile Val Gln Gln Gln Ser Asn Leu Leu Lys Ala Ile Glu Ala
1               5                   10                  15

Gln Gln His Leu Leu Lys Leu Thr Val Trp Gly Ile Lys Gln Leu Gln
            20                  25                  30

Ala Arg Val Leu Ala Val Glu Arg Tyr Leu Lys Asp Gln
        35                  40                  45

<210> SEQ ID NO 33
<211> LENGTH: 36
<212> TYPE: PRT
<213> ORGANISM: Artificial Sequence
<220> FEATURE:
<223> OTHER INFORMATION: Description of Artificial Sequence:Synthetic

<400> SEQUENCE: 33

Ser Gly Ile Val Gln Gln Gln Ser Asn Leu Leu Lys Ala Ile Glu Ala
1               5                   10                  15

Gln Gln His Leu Leu Lys Leu Thr Val Trp Gly Ile Lys Gln Leu Gln
            20                  25                  30

Ala Arg Val Leu
        35

<210> SEQ ID NO 34
<211> LENGTH: 38
<212> TYPE: PRT
<213> ORGANISM: Artificial Sequence
<220> FEATURE:
<223> OTHER INFORMATION: Description of Artificial Sequence:Synthetic

<400> SEQUENCE: 34

Ser Asn Leu Leu Lys Ala Ile Glu Ala Gln Gln His Leu Leu Lys Leu
1               5                   10                  15

-continued

Thr Val Trp Gly Ile Lys Gln Leu Gln Ala Arg Val Leu Ala Val Glu
              20                  25                  30

Arg Tyr Leu Lys Asp Gln
        35

<210> SEQ ID NO 35
<211> LENGTH: 45
<212> TYPE: PRT
<213> ORGANISM: Artificial Sequence
<220> FEATURE:
<223> OTHER INFORMATION: Description of Artificial Sequence:Synthetic

<400> SEQUENCE: 35

Ser Gly Ile Val Gln Gln Gln Asn Ile Leu Leu Arg Ala Ile Glu Ala
 1               5                  10                  15

Gln Gln His Leu Leu Gln Leu Ser Ile Trp Gly Ile Lys Gln Leu Gln
             20                  25                  30

Ala Lys Val Leu Ala Ile Glu Arg Tyr Leu Arg Asp Gln
         35                  40                  45

<210> SEQ ID NO 36
<211> LENGTH: 36
<212> TYPE: PRT
<213> ORGANISM: Artificial Sequence
<220> FEATURE:
<223> OTHER INFORMATION: Description of Artificial Sequence:Synthetic

<400> SEQUENCE: 36

Ser Gly Ile Val Gln Gln Gln Asn Ile Leu Leu Arg Ala Ile Glu Ala
 1               5                  10                  15

Gln Gln His Leu Leu Gln Leu Ser Ile Trp Gly Ile Lys Gln Leu Gln
             20                  25                  30

Ala Lys Val Leu
         35

<210> SEQ ID NO 37
<211> LENGTH: 38
<212> TYPE: PRT
<213> ORGANISM: Artificial Sequence
<220> FEATURE:
<223> OTHER INFORMATION: Description of Artificial Sequence:Synthetic

<400> SEQUENCE: 37

Asn Ile Leu Leu Arg Ala Ile Glu Ala Gln Gln His Leu Leu Gln Leu
 1               5                  10                  15

Ser Ile Trp Gly Ile Lys Gln Leu Gln Ala Lys Val Leu Ala Ile Glu
             20                  25                  30

Arg Tyr Leu Arg Asp Gln
        35

<210> SEQ ID NO 38
<211> LENGTH: 45
<212> TYPE: PRT
<213> ORGANISM: Artificial Sequence
<220> FEATURE:
<223> OTHER INFORMATION: Description of Artificial Sequence:Synthetic

<400> SEQUENCE: 38

Lys Gly Ile Val Gln Gln Gln Asp Asn Leu Leu Arg Ala Ile Gln Ala
 1               5                  10                  15

Gln Gln Gln Leu Leu Arg Leu Ser Xaa Trp Gly Ile Arg Gln Leu Arg
             20                  25                  30

Ala Arg Leu Leu Ala Leu Glu Thr Leu Leu Gln Asn Gln
            35                  40                  45

<210> SEQ ID NO 39
<211> LENGTH: 35
<212> TYPE: PRT
<213> ORGANISM: Artificial Sequence
<220> FEATURE:
<223> OTHER INFORMATION: Description of Artificial Sequence:Synthetic

<400> SEQUENCE: 39

Lys Gly Ile Val Gln Gln Gln Asp Asn Leu Leu Arg Ala Ile Gln Ala
  1               5                  10                  15

Gln Gln Gln Leu Leu Arg Leu Ser Xaa Trp Gly Ile Arg Gln Leu Arg
             20                  25                  30

Ala Arg Leu
        35

<210> SEQ ID NO 40
<211> LENGTH: 38
<212> TYPE: PRT
<213> ORGANISM: Artificial Sequence
<220> FEATURE:
<223> OTHER INFORMATION: Description of Artificial Sequence:Synthetic

<400> SEQUENCE: 40

Asp Asn Leu Leu Arg Ala Ile Gln Ala Gln Gln Leu Leu Arg Leu
  1               5                  10                  15

Ser Xaa Trp Gly Ile Arg Gln Leu Arg Ala Arg Leu Leu Ala Leu Glu
             20                  25                  30

Thr Leu Leu Gln Asn Gln
        35

<210> SEQ ID NO 41
<211> LENGTH: 46
<212> TYPE: PRT
<213> ORGANISM: Artificial Sequence
<220> FEATURE:
<223> OTHER INFORMATION: Description of Artificial Sequence:Synthetic

<400> SEQUENCE: 41

Trp Met Glu Trp Asp Arg Glu Ile Asn Asn Tyr Thr Ser Leu Ile His
  1               5                  10                  15

Ser Leu Ile Glu Glu Ser Gln Asn Gln Gln Glu Lys Asn Glu Gln Glu
             20                  25                  30

Leu Leu Glu Leu Asp Lys Trp Ala Ser Leu Trp Asn Trp Phe
        35                  40                  45

<210> SEQ ID NO 42
<211> LENGTH: 46
<212> TYPE: PRT
<213> ORGANISM: Artificial Sequence
<220> FEATURE:
<223> OTHER INFORMATION: Description of Artificial Sequence:Synthetic

<400> SEQUENCE: 42

Trp Met Glu Trp Glu Arg Glu Ile Glu Asn Tyr Thr Gly Leu Ile Tyr
  1               5                  10                  15

Thr Leu Ile Glu Glu Ser Gln Asn Gln Gln Glu Lys Asn Glu Gln Asp
             20                  25                  30

Leu Leu Ala Leu Asp Lys Trp Ala Ser Leu Trp Asn Trp Phe
        35                  40                  45

<210> SEQ ID NO 43
<211> LENGTH: 34
<212> TYPE: PRT
<213> ORGANISM: Artificial Sequence
<220> FEATURE:
<223> OTHER INFORMATION: Description of Artificial Sequence:Synthetic

<400> SEQUENCE: 43

Trp Met Glu Trp Glu Arg Glu Ile Glu Asn Tyr Thr Gly Leu Ile Tyr
 1               5                  10                  15

Thr Leu Ile Glu Glu Ser Gln Asn Gln Gln Glu Lys Asn Glu Gln Asp
            20                  25                  30

Leu Leu

<210> SEQ ID NO 44
<211> LENGTH: 36
<212> TYPE: PRT
<213> ORGANISM: Artificial Sequence
<220> FEATURE:
<223> OTHER INFORMATION: Description of Artificial Sequence:Synthetic

<400> SEQUENCE: 44

Tyr Thr Gly Leu Ile Tyr Thr Leu Ile Glu Glu Ser Gln Asn Gln Gln
 1               5                  10                  15

Glu Lys Asn Glu Gln Asp Leu Leu Ala Leu Asp Lys Trp Ala Ser Leu
            20                  25                  30

Trp Asn Trp Phe
        35

<210> SEQ ID NO 45
<211> LENGTH: 46
<212> TYPE: PRT
<213> ORGANISM: Artificial Sequence
<220> FEATURE:
<223> OTHER INFORMATION: Description of Artificial Sequence:Synthetic

<400> SEQUENCE: 45

Trp Met Glu Trp Glu Arg Glu Ile Asp Asn Tyr Thr Ser Glu Ile Tyr
 1               5                  10                  15

Thr Leu Ile Glu Glu Ser Gln Asn Gln Gln Glu Lys Asn Glu Gln Glu
            20                  25                  30

Leu Leu Glu Leu Asp Lys Trp Ala Ser Leu Trp Asn Trp Phe
        35                  40                  45

<210> SEQ ID NO 46
<211> LENGTH: 34
<212> TYPE: PRT
<213> ORGANISM: Artificial Sequence
<220> FEATURE:
<223> OTHER INFORMATION: Description of Artificial Sequence:Synthetic

<400> SEQUENCE: 46

Trp Met Glu Trp Glu Arg Glu Ile Asp Asn Tyr Thr Ser Glu Ile Tyr
 1               5                  10                  15

Thr Leu Ile Glu Glu Ser Gln Asn Gln Gln Glu Lys Asn Glu Gln Glu
            20                  25                  30

Leu Leu

<210> SEQ ID NO 47
<211> LENGTH: 36
<212> TYPE: PRT
<213> ORGANISM: Artificial Sequence

```
<220> FEATURE:
<223> OTHER INFORMATION: Description of Artificial Sequence:Synthetic

<400> SEQUENCE: 47

Tyr Thr Ser Glu Ile Tyr Thr Leu Ile Glu Glu Ser Gln Asn Gln Gln
  1               5                  10                  15

Glu Lys Asn Glu Gln Glu Leu Leu Glu Leu Asp Lys Trp Ala Ser Leu
             20                  25                  30

Trp Asn Trp Phe
         35

<210> SEQ ID NO 48
<211> LENGTH: 46
<212> TYPE: PRT
<213> ORGANISM: Artificial Sequence
<220> FEATURE:
<223> OTHER INFORMATION: Description of Artificial Sequence:Synthetic

<400> SEQUENCE: 48

Trp Met Glu Trp Glu Arg Glu Ile Asp Asn Tyr Thr Asp Tyr Ile Tyr
  1               5                  10                  15

Asp Leu Leu Glu Lys Ser Gln Thr Gln Gln Lys Asn Glu Lys Glu
             20                  25                  30

Leu Leu Glu Leu Asp Lys Trp Ala Ser Leu Trp Asn Trp Phe
         35                  40                  45

<210> SEQ ID NO 49
<211> LENGTH: 34
<212> TYPE: PRT
<213> ORGANISM: Artificial Sequence
<220> FEATURE:
<223> OTHER INFORMATION: Description of Artificial Sequence:Synthetic

<400> SEQUENCE: 49

Trp Met Glu Trp Glu Arg Glu Ile Asp Asn Tyr Thr Asp Tyr Ile Tyr
  1               5                  10                  15

Asp Leu Leu Glu Lys Ser Gln Thr Gln Gln Glu Lys Asn Glu Lys Glu
             20                  25                  30

Leu Leu

<210> SEQ ID NO 50
<211> LENGTH: 36
<212> TYPE: PRT
<213> ORGANISM: Artificial Sequence
<220> FEATURE:
<223> OTHER INFORMATION: Description of Artificial Sequence:Synthetic

<400> SEQUENCE: 50

Tyr Thr Asp Tyr Ile Tyr Asp Leu Leu Glu Lys Ser Gln Thr Gln Gln
  1               5                  10                  15

Glu Lys Asn Glu Lys Glu Leu Leu Glu Leu Asp Lys Trp Ala Ser Leu
             20                  25                  30

Trp Asn Trp Phe
         35

<210> SEQ ID NO 51
<211> LENGTH: 46
<212> TYPE: PRT
<213> ORGANISM: Artificial Sequence
<220> FEATURE:
<223> OTHER INFORMATION: Description of Artificial Sequence:Synthetic

<400> SEQUENCE: 51
```

```
Trp Ile Gln Trp Asp Arg Glu Ile Ser Asn Tyr Thr Gly Ile Ile Tyr
  1               5                  10                  15

Arg Leu Leu Glu Glu Ser Gln Asn Gln Gln Glu Asn Asn Glu Lys Asp
             20                  25                  30

Leu Leu Ala Leu Asp Lys Trp Gln Asn Leu Trp Ser Trp Phe
         35                  40                  45
```

<210> SEQ ID NO 52
<211> LENGTH: 34
<212> TYPE: PRT
<213> ORGANISM: Artificial Sequence
<220> FEATURE:
<223> OTHER INFORMATION: Description of Artificial Sequence:Synthetic

<400> SEQUENCE: 52

```
Trp Ile Gln Trp Asp Arg Glu Ile Ser Asn Tyr Thr Gly Ile Ile Tyr
  1               5                  10                  15

Arg Leu Leu Glu Glu Ser Gln Asn Gln Gln Glu Asn Asn Glu Lys Asp
             20                  25                  30

Leu Leu
```

<210> SEQ ID NO 53
<211> LENGTH: 36
<212> TYPE: PRT
<213> ORGANISM: Artificial Sequence
<220> FEATURE:
<223> OTHER INFORMATION: Description of Artificial Sequence:Synthetic

<400> SEQUENCE: 53

```
Tyr Thr Gly Ile Ile Tyr Arg Leu Leu Glu Glu Ser Gln Asn Gln Gln
  1               5                  10                  15

Glu Asn Asn Glu Lys Asp Leu Leu Ala Leu Asp Lys Trp Gln Asn Leu
             20                  25                  30

Trp Ser Trp Phe
         35
```

<210> SEQ ID NO 54
<211> LENGTH: 46
<212> TYPE: PRT
<213> ORGANISM: Artificial Sequence
<220> FEATURE:
<223> OTHER INFORMATION: Description of Artificial Sequence:Synthetic

<400> SEQUENCE: 54

```
Trp Met Glu Trp Glu Arg Glu Ile Ser Asn Tyr Thr Gly Leu Ile Tyr
  1               5                  10                  15

Asp Leu Ile Glu Glu Ser Gln Ile Gln Gln Glu Lys Asn Glu Lys Asp
             20                  25                  30

Leu Leu Glu Leu Asp Lys Trp Ala Ser Leu Trp Asn Trp Phe
         35                  40                  45
```

<210> SEQ ID NO 55
<211> LENGTH: 34
<212> TYPE: PRT
<213> ORGANISM: Artificial Sequence
<220> FEATURE:
<223> OTHER INFORMATION: Description of Artificial Sequence:Synthetic

<400> SEQUENCE: 55

```
Trp Met Glu Trp Glu Arg Glu Ile Ser Asn Tyr Thr Gly Leu Ile Tyr
  1               5                  10                  15
```

Asp Leu Ile Glu Glu Ser Gln Ile Gln Gln Glu Lys Asn Glu Lys Asp
            20                  25                  30

Leu Leu

<210> SEQ ID NO 56
<211> LENGTH: 36
<212> TYPE: PRT
<213> ORGANISM: Artificial Sequence
<220> FEATURE:
<223> OTHER INFORMATION: Description of Artificial Sequence:Synthetic

<400> SEQUENCE: 56

Tyr Thr Gly Leu Ile Tyr Asp Leu Ile Glu Glu Ser Gln Ile Gln Gln
 1               5                  10                  15

Glu Lys Asn Glu Lys Asp Leu Leu Glu Leu Asp Lys Trp Ala Ser Leu
            20                  25                  30

Trp Asn Trp Phe
        35

<210> SEQ ID NO 57
<211> LENGTH: 46
<212> TYPE: PRT
<213> ORGANISM: Artificial Sequence
<220> FEATURE:
<223> OTHER INFORMATION: Description of Artificial Sequence:Synthetic

<400> SEQUENCE: 57

Trp Met Glu Trp Gln Lys Glu Ile Ser Asn Tyr Ser Asn Glu Val Tyr
 1               5                  10                  15

Arg Leu Ile Glu Lys Ser Gln Asn Gln Glu Lys Asn Glu Gln Gly
            20                  25                  30

Leu Leu Ala Leu Asp Lys Trp Ala Ser Leu Trp Asn Trp Phe
        35                  40                  45

<210> SEQ ID NO 58
<211> LENGTH: 34
<212> TYPE: PRT
<213> ORGANISM: Artificial Sequence
<220> FEATURE:
<223> OTHER INFORMATION: Description of Artificial Sequence:Synthetic

<400> SEQUENCE: 58

Trp Met Glu Trp Gln Lys Glu Ile Ser Asn Tyr Ser Asn Glu Val Tyr
 1               5                  10                  15

Arg Leu Ile Glu Lys Ser Gln Asn Gln Gln Glu Lys Asn Glu Gln Gly
            20                  25                  30

Leu Leu

<210> SEQ ID NO 59
<211> LENGTH: 36
<212> TYPE: PRT
<213> ORGANISM: Artificial Sequence
<220> FEATURE:
<223> OTHER INFORMATION: Description of Artificial Sequence:Synthetic

<400> SEQUENCE: 59

Tyr Ser Asn Glu Val Tyr Arg Leu Ile Glu Lys Ser Gln Asn Gln Gln
 1               5                  10                  15

Glu Lys Asn Glu Gln Gly Leu Leu Ala Leu Asp Lys Trp Ala Ser Leu
            20                  25                  30

Trp Asn Trp Phe
        35

<210> SEQ ID NO 60
<211> LENGTH: 46
<212> TYPE: PRT
<213> ORGANISM: Artificial Sequence
<220> FEATURE:
<223> OTHER INFORMATION: Description of Artificial Sequence:Synthetic

<400> SEQUENCE: 60

Trp Ile Gln Trp Asp Arg Glu Ile Ser Asn Tyr Thr Gln Gln Ile Tyr
1               5                   10                  15

Ser Leu Ile Glu Glu Ser Gln Asn Gln Gln Glu Lys Asn Glu Gln Asp
            20                  25                  30

Leu Leu Ala Leu Asp Asn Trp Ala Ser Leu Trp Thr Trp Phe
        35                  40                  45

<210> SEQ ID NO 61
<211> LENGTH: 34
<212> TYPE: PRT
<213> ORGANISM: Artificial Sequence
<220> FEATURE:
<223> OTHER INFORMATION: Description of Artificial Sequence:Synthetic

<400> SEQUENCE: 61

Trp Ile Gln Trp Asp Arg Glu Ile Ser Asn Tyr Thr Gln Gln Ile Tyr
1               5                   10                  15

Ser Leu Ile Glu Glu Ser Gln Asn Gln Gln Glu Lys Asn Glu Gln Asp
            20                  25                  30

Leu Leu

<210> SEQ ID NO 62
<211> LENGTH: 36
<212> TYPE: PRT
<213> ORGANISM: Artificial Sequence
<220> FEATURE:
<223> OTHER INFORMATION: Description of Artificial Sequence:Synthetic

<400> SEQUENCE: 62

Tyr Thr Gln Gln Ile Tyr Ser Leu Ile Glu Glu Ser Gln Asn Gln Gln
1               5                   10                  15

Glu Lys Asn Glu Gln Asp Leu Leu Ala Leu Asp Asn Trp Ala Ser Leu
            20                  25                  30

Trp Thr Trp Phe
        35

<210> SEQ ID NO 63
<211> LENGTH: 46
<212> TYPE: PRT
<213> ORGANISM: Artificial Sequence
<220> FEATURE:
<223> OTHER INFORMATION: Description of Artificial Sequence:Synthetic

<400> SEQUENCE: 63

Trp Met Glu Trp Asp Arg Gln Ile Asp Asn Tyr Thr Glu Val Ile Tyr
1               5                   10                  15

Arg Leu Leu Glu Leu Ser Gln Thr Gln Gln Glu Gln Asn Glu Gln Asp
            20                  25                  30

Leu Leu Ala Leu Asp Lys Trp Asp Ser Leu Trp Asn Trp Phe
        35                  40                  45

<210> SEQ ID NO 64
<211> LENGTH: 34

<212> TYPE: PRT
<213> ORGANISM: Artificial Sequence
<220> FEATURE:
<223> OTHER INFORMATION: Description of Artificial Sequence:Synthetic

<400> SEQUENCE: 64

Trp Met Glu Trp Asp Arg Gln Ile Asp Asn Tyr Thr Glu Val Ile Tyr
1               5                   10                  15

Arg Leu Leu Glu Leu Ser Gln Thr Gln Gln Glu Gln Asn Glu Gln Asp
            20                  25                  30

Leu Leu

<210> SEQ ID NO 65
<211> LENGTH: 36
<212> TYPE: PRT
<213> ORGANISM: Artificial Sequence
<220> FEATURE:
<223> OTHER INFORMATION: Description of Artificial Sequence:Synthetic

<400> SEQUENCE: 65

Tyr Thr Glu Val Ile Tyr Arg Leu Leu Glu Leu Ser Gln Thr Gln Gln
1               5                   10                  15

Glu Gln Asn Glu Gln Asp Leu Leu Ala Leu Asp Lys Trp Asp Ser Leu
            20                  25                  30

Trp Asn Trp Phe
        35

<210> SEQ ID NO 66
<211> LENGTH: 47
<212> TYPE: PRT
<213> ORGANISM: Artificial Sequence
<220> FEATURE:
<223> OTHER INFORMATION: Description of Artificial Sequence:Synthetic

<400> SEQUENCE: 66

Trp Ile Gln Trp Glu Arg Glu Ile Asn Asn Tyr Thr Gly Ile Ile Tyr
1               5                   10                  15

Ser Leu Ile Glu Glu Ala Gln Asn Gln Gln Glu Asn Asn Glu Lys Asp
            20                  25                  30

Leu Leu Ala Leu Asp Lys Trp Thr Asn Leu Trp Asn Trp Phe Asn
        35                  40                  45

<210> SEQ ID NO 67
<211> LENGTH: 34
<212> TYPE: PRT
<213> ORGANISM: Artificial Sequence
<220> FEATURE:
<223> OTHER INFORMATION: Description of Artificial Sequence:Synthetic

<400> SEQUENCE: 67

Trp Ile Gln Trp Glu Arg Glu Ile Asn Asn Tyr Thr Gly Ile Ile Tyr
1               5                   10                  15

Ser Leu Ile Glu Glu Ala Gln Asn Gln Gln Glu Asn Asn Glu Lys Asp
            20                  25                  30

Leu Leu

<210> SEQ ID NO 68
<211> LENGTH: 37
<212> TYPE: PRT
<213> ORGANISM: Artificial Sequence
<220> FEATURE:
<223> OTHER INFORMATION: Description of Artificial Sequence:Synthetic

```
<400> SEQUENCE: 68

Tyr Thr Gly Ile Ile Tyr Ser Leu Ile Glu Glu Ala Gln Asn Gln Gln
 1               5                  10                  15

Glu Asn Asn Glu Lys Asp Leu Leu Ala Leu Asp Lys Trp Thr Asn Leu
            20                  25                  30

Trp Asn Trp Phe Asn
        35

<210> SEQ ID NO 69
<211> LENGTH: 46
<212> TYPE: PRT
<213> ORGANISM: Artificial Sequence
<220> FEATURE:
<223> OTHER INFORMATION: Description of Artificial Sequence:Synthetic

<400> SEQUENCE: 69

Trp Gln Gln Trp Asp Glu Lys Val Arg Asn Tyr Ser Gly Val Ile Phe
 1               5                  10                  15

Gly Leu Ile Glu Gln Ala Gln Glu Gln Gln Asn Thr Asn Glu Lys Ser
            20                  25                  30

Leu Leu Glu Leu Asp Gln Trp Asp Ser Leu Trp Ser Trp Phe
        35                  40                  45

<210> SEQ ID NO 70
<211> LENGTH: 34
<212> TYPE: PRT
<213> ORGANISM: Artificial Sequence
<220> FEATURE:
<223> OTHER INFORMATION: Description of Artificial Sequence:Synthetic

<400> SEQUENCE: 70

Trp Gln Gln Trp Asp Glu Lys Val Arg Asn Tyr Ser Gly Val Ile Phe
 1               5                  10                  15

Gly Leu Ile Glu Gln Ala Gln Glu Gln Gln Asn Thr Asn Glu Lys Ser
            20                  25                  30

Leu Leu

<210> SEQ ID NO 71
<211> LENGTH: 36
<212> TYPE: PRT
<213> ORGANISM: Artificial Sequence
<220> FEATURE:
<223> OTHER INFORMATION: Description of Artificial Sequence:Synthetic

<400> SEQUENCE: 71

Tyr Ser Gly Val Ile Phe Gly Leu Ile Glu Gln Ala Gln Glu Gln Gln
 1               5                  10                  15

Asn Thr Asn Glu Lys Ser Leu Leu Glu Leu Asp Gln Trp Asp Ser Leu
            20                  25                  30

Trp Ser Trp Phe
        35

<210> SEQ ID NO 72
<211> LENGTH: 46
<212> TYPE: PRT
<213> ORGANISM: Artificial Sequence
<220> FEATURE:
<223> OTHER INFORMATION: Description of Artificial Sequence:Synthetic

<400> SEQUENCE: 72

Trp Gln Glu Trp Asp Arg Gln Ile Ser Asn Ile Ser Ser Thr Ile Tyr
 1               5                  10                  15
```

Glu Glu Ile Gln Lys Ala Gln Val Gln Gln Glu Gln Asn Lys Lys
            20                  25                  30

Leu Leu Glu Leu Asp Glu Trp Ala Ser Ile Trp Asn Trp Leu
        35                  40                  45

<210> SEQ ID NO 73
<211> LENGTH: 34
<212> TYPE: PRT
<213> ORGANISM: Artificial Sequence
<220> FEATURE:
<223> OTHER INFORMATION: Description of Artificial Sequence:Synthetic

<400> SEQUENCE: 73

Trp Gln Glu Trp Asp Arg Gln Ile Ser Asn Ile Ser Ser Thr Ile Tyr
 1               5                  10                  15

Glu Glu Ile Gln Lys Ala Gln Val Gln Gln Glu Gln Asn Glu Lys Lys
            20                  25                  30

Leu Leu

<210> SEQ ID NO 74
<211> LENGTH: 36
<212> TYPE: PRT
<213> ORGANISM: Artificial Sequence
<220> FEATURE:
<223> OTHER INFORMATION: Description of Artificial Sequence:Synthetic

<400> SEQUENCE: 74

Ile Ser Ser Thr Ile Tyr Glu Glu Ile Gln Lys Ala Gln Val Gln Gln
 1               5                  10                  15

Glu Gln Asn Glu Lys Lys Leu Leu Glu Leu Asp Glu Trp Ala Ser Ile
            20                  25                  30

Trp Asn Trp Leu
        35

<210> SEQ ID NO 75
<211> LENGTH: 465
<212> TYPE: DNA
<213> ORGANISM: Artificial Sequence
<220> FEATURE:
<221> NAME/KEY: CDS
<222> LOCATION: (34)..(357)
<220> FEATURE:
<223> OTHER INFORMATION: Description of Artificial Sequence:Synthetic

<400> SEQUENCE: 75
agcggtgcgc cgaaagtacg cgctaagctt cat atg ggt att gtt cag cag cag      54
                                   Met Gly Ile Val Gln Gln Gln
                                    1               5 aac aat ttg ctg agg gct att gag gcg caa cag cac ctg ctg cag ctg      102
Asn Asn Leu Leu Arg Ala Ile Glu Ala Gln Gln His Leu Leu Gln Leu
            10                  15                  20 acc gta tgg ggc atc aag cag ctg cag gca cgc atc ctg gct gtt gaa      150
Thr Val Trp Gly Ile Lys Gln Leu Gln Ala Arg Ile Leu Ala Val Glu
        25                  30                  35 cgc tac ctg aag gat caa ggc ggc ggc tca ggc gcc ggc tca gag tgg      198
Arg Tyr Leu Lys Asp Gln Gly Gly Gly Ser Gly Ala Gly Ser Glu Trp
 40                  45                  50                  55 gac aga gaa att aac aat tac aca agc tta ata cac tcc tta att gaa      246
Asp Arg Glu Ile Asn Asn Tyr Thr Ser Leu Ile His Ser Leu Ile Glu
                60                  65                  70 gaa tcg caa aac cag caa gaa aag aat gaa caa gaa tta ttg gaa tta      294
Glu Ser Gln Asn Gln Gln Glu Lys Asn Glu Gln Glu Leu Leu Glu Leu

```
                    75                  80                  85
gat aaa tgg gca agt ttg tgg aat tgg ttt gaa ttc atc gat gat atc        342
Asp Lys Trp Ala Ser Leu Trp Asn Trp Phe Glu Phe Ile Asp Asp Ile
            90                  95                 100 aga tcc ggc tgc taa caaagcccga aggaagctg agtttggctg ctgccacccg         397
Arg Ser Gly Cys
        105 ctgagcaata actagcataa ccccttgggg gcctctaaac gggtcttgag gggttttttg      457 cttgaaag                                                               465

<210> SEQ ID NO 76
<211> LENGTH: 107
<212> TYPE: PRT
<213> ORGANISM: Artificial Sequence
<220> FEATURE:
<223> OTHER INFORMATION: Description of Artificial Sequence:Synthetic

<400> SEQUENCE: 76

Met Gly Ile Val Gln Gln Asn Asn Leu Leu Arg Ala Ile Glu Ala
 1               5                  10                  15

Gln Gln His Leu Leu Gln Leu Thr Val Trp Gly Ile Lys Gln Leu Gln
            20                  25                  30

Ala Arg Ile Leu Ala Val Glu Arg Tyr Leu Lys Asp Gln Gly Gly Gly
        35                  40                  45

Ser Gly Ala Gly Ser Glu Trp Asp Arg Glu Ile Asn Asn Tyr Thr Ser
    50                  55                  60

Leu Ile His Ser Leu Ile Glu Glu Ser Gln Asn Gln Gln Glu Lys Asn
65                  70                  75                  80

Glu Gln Glu Leu Leu Glu Leu Asp Lys Trp Ala Ser Leu Trp Asn Trp
                85                  90                  95

Phe Glu Phe Ile Asp Asp Ile Arg Ser Gly Cys
            100                 105

<210> SEQ ID NO 77
<211> LENGTH: 197
<212> TYPE: DNA
<213> ORGANISM: Artificial Sequence
<220> FEATURE:
<223> OTHER INFORMATION: Description of Artificial Sequence:Synthetic

<400> SEQUENCE: 77
gagggactat atccggttat tcacaaggac ggctgtgggc gccatgatcg cgtagtcgat      60
agtggctcca agtaaccgga agcgacaggg actgtgccgg gcgccaaagg cggtcgacag     120
tgctttctag aaccgggtgc gcataaaaat gcatcacgcc tatagcgcta gagccgctgc     180
attaaatgaa tcggcca                                                    197

<210> SEQ ID NO 78
<211> LENGTH: 18
<212> TYPE: PRT
<213> ORGANISM: Artificial Sequence
<220> FEATURE:
<223> OTHER INFORMATION: Description of Artificial Sequence:Synthetic

<400> SEQUENCE: 78

Tyr Thr Ser Leu Ile His Ser Leu Ile Glu Glu Ser Gln Asn Gln Gln
 1               5                  10                  15

Glu Lys
```

```
<210> SEQ ID NO 79
<211> LENGTH: 18
<212> TYPE: PRT
<213> ORGANISM: Artificial Sequence
<220> FEATURE:
<223> OTHER INFORMATION: Description of Artificial Sequence:Synthetic

<400> SEQUENCE: 79

Glu Glu Ser Gln Asn Gln Gln Glu Lys Asn Glu Gln Glu Leu Leu Glu
 1               5                  10                  15

Leu Asp

<210> SEQ ID NO 80
<211> LENGTH: 13
<212> TYPE: PRT
<213> ORGANISM: Artificial Sequence
<220> FEATURE:
<223> OTHER INFORMATION: Description of Artificial Sequence:Synthetic

<400> SEQUENCE: 80

Leu Glu Leu Asp Lys Trp Ala Ser Leu Trp Asn Trp Phe
 1               5                  10

<210> SEQ ID NO 81
<211> LENGTH: 26
<212> TYPE: PRT
<213> ORGANISM: Artificial Sequence
<220> FEATURE:
<223> OTHER INFORMATION: Description of Artificial Sequence:Synthetic

<400> SEQUENCE: 81

Gly Gly Gly Cys Cys Cys Ala Thr Ala Thr Gly Gly Gly Thr Ala Thr
 1               5                  10                  15

Thr Gly Thr Thr Cys Ala Gly Cys Ala Gly
             20                  25

<210> SEQ ID NO 82
<211> LENGTH: 44
<212> TYPE: PRT
<213> ORGANISM: Artificial Sequence
<220> FEATURE:
<223> OTHER INFORMATION: Description of Artificial Sequence:Synthetic

<400> SEQUENCE: 82

Gly Gly Gly Cys Cys Gly Gly Cys Gly Cys Cys Thr Gly Ala Gly Cys
 1               5                  10                  15

Cys Gly Cys Cys Gly Cys Cys Thr Thr Gly Ala Thr Cys Cys Thr Thr
             20                  25                  30

Cys Ala Gly Gly Thr Ala Gly Cys Gly Thr Thr Cys
         35                  40

<210> SEQ ID NO 83
<211> LENGTH: 44
<212> TYPE: PRT
<213> ORGANISM: Artificial Sequence
<220> FEATURE:
<223> OTHER INFORMATION: Description of Artificial Sequence:Synthetic

<400> SEQUENCE: 83

Gly Gly Gly Cys Cys Gly Gly Cys Gly Cys Cys Gly Gly Cys Thr Cys
 1               5                  10                  15

Ala Gly Ala Gly Thr Gly Gly Gly Ala Cys Ala Gly Ala Gly Ala Ala
             20                  25                  30

Ala Thr Thr Ala Ala Cys Ala Ala Thr Thr Ala Cys
```

-continued

```
                35                  40

<210> SEQ ID NO 84
<211> LENGTH: 41
<212> TYPE: PRT
<213> ORGANISM: Artificial Sequence
<220> FEATURE:
<223> OTHER INFORMATION: Description of Artificial Sequence:Synthetic

<400> SEQUENCE: 84

Gly Gly Gly Cys Cys Gly Ala Ala Thr Thr Cys Thr Thr Ala Ala Ala
  1               5                  10                  15

Ala Cys Cys Ala Ala Thr Thr Cys Cys Ala Cys Ala Ala Ala Cys Thr
                20                  25                  30

Thr Gly Cys Cys Ala Thr Thr Thr
                35                  40
```

What is claimed is:

1. A conjugate polypeptide formed from two or more amino acid sequences that comprise:
    (a) a first gp41 polypeptide having an amino acid sequence corresponding to a polypeptide comprising the amino acid sequence of SEQ ID NO:2 or SEQ ID NO:3 and is capable of forming a stable coiled-coil structure; and
    (b) a second gp41 polypeptide having an amino acid sequence corresponding to a polypeptide comprising the amino acid sequence of SEQ ID NO:5 or SEQ ID NO:6 and is capable of forming an amphipathic α helical segment;
    wherein at least three polypeptides of (a) and (b) are alternately linked to one another via a peptide bond to form the conjugate polypeptide or at least two polypeptides of (a) and (b) are linked by an amino acid linking sequence consisting of about 2 to about 25 amino acids to form the conjugate polypeptides.

2. The conjugate of claim 1, wherein:
    said first gp41 polypeptide comprises about at least 28 amino acids of the following sequence: ARQLLSGIVQQQNNLL-RAIEAQQHLLQLTVWGIKQLQARILA-VERYLKDQQLLGI (SEQ. ID NO: 1), or multimers thereof; and
    said second gp41 polypeptide comprises about at least 24 amino acids of the following sequence: WNNMTWMEWDREINNYTSLIH-SLIEESQNQQEKNEQELLELDKWASLWNWFNI TNW (SEQ ID NO:4), or multimers thereof.

3. The conjugate of claim 1, wherein:
    said first gp41 polypeptide is selected from the group consisting of SEQ ID NO: 1, SEQ ID NO: 2, SEQ ID NO: 3, and one of SEQ ID NO: 9 through SEQ ID NO: 40, and wherein the peptide can be optionally coupled to a larger carrier protein, or optionally include a terminal protecting group at the N- and/or C-termini; and
    said second gp41 polypeptide is selected from the group consisting of SEQ ID NO: 4, SEQ ID NO: 5, SEQ ID NO: 6, and one of SEQ ID NO: 41 through SEQ ID NO: 74, and wherein the peptide can be optionally coupled to a larger carrier protein, or optionally include a terminal protecting group at the N- and/or C-termini.

4. A composition comprising a conjugate of claim 1, and a physiologically acceptable carrier.

5. A method of raising a neutralizing antibody response to HIV comprising:
    administering to a mammal a composition including at least one conjugate polypeptide of claim 1;
    and detecting the presence of a neutralizing antibody response to HIV.

6. The method of claim 5, wherein said conjugate polypeptide comprises an amino acid linking sequence having the amino acid sequence of (GGGGS)$_3$(SEQ ID NO:7).

7. The method of claim 5, wherein said conjugate polypeptide comprises a) a first gp41 polypeptide having the amino acid sequence of SEQ ID NO:2 or 3 and b) a second gp41 polypeptide having the amino acid sequence of SEQ ID NO:5 or SEQ ID NO:6.

8. The method of claim 7, wherein the sequence of (a) is linked to a sequence of (b) which is linked to a second sequence of (a).

9. The method of claim 7, wherein a sequence of (b) is linked to a sequence of (a) which is linked to a second sequence of (b).

10. The method of claim 7, wherein said one or more sequences is one of (a) and (b), and wherein said first or second gp41 polypeptides are coupled to a larger carrier protein.

11. A conjugate polypeptide formed from two or more amino acid sequences that comprise:
    (a) a first naturally occurring gp41 polypeptide having an amino acid sequence corresponding to a polypeptide comprising the amino acid sequence of SEQ ID NO:2 or SEQ ID NO:3; and
    (b) a second naturally occurring gp41 polypeptide having an amino acid sequence corresponding to a polypeptide comprising the amino acid sequence of SEQ ID NO:5 or SEQ ID NO:6;
    wherein
    at least three polypeptides of (a) and (b) are alternately linked to one another via a peptide bond to form the conjugate polypeptide, or at least two polypeptides of (a) and (b) are linked by an amino acid linking sequence consisting of about 2 to about 25 amino acids to form the conjugate polypeptide.

12. The conjugate polypeptide of claim 1 or claim 11, wherein the first polypeptide comprises the amino acid sequence of SEQ ID NO:3 and the second polypeptide comprises the amino acid sequence of SEQ ID NO:6.

13. The conjugate polypeptide of claim 1 or claim 11, wherein the first polypeptide comprises the amino acid sequence of SEQ ID NO:2 and the second polypeptide comprises the amino acid sequence of SEQ ID NO:5.

14. The conjugate polypeptide of claim 1 or claim 11, wherein the sequence of (a) is linked to a sequence of (b) which is linked to a second sequence of (a).

15. The conjugate polypeptide of claim 1 or claim 11, wherein a sequence of (b) is linked to a sequence of (a) which is linked to a second sequence of (b).

16. The conjugate polypeptide of claim 1 or claim 11, wherein said first and second polypeptides are (a) and (b), and wherein said at least one of said first and second polypeptides are coupled to a larger carrier protein.

* * * * *